US006930085B2

(12) United States Patent
Fogelman et al.

(10) Patent No.: US 6,930,085 B2
(45) Date of Patent: Aug. 16, 2005

(54) G-TYPE PEPTIDES TO AMELIORATE ATHEROSCLEROSIS

(75) Inventors: Alan M. Fogelman, Beverly Hills, CA (US); Mohamad Navab, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/120,508

(22) Filed: Apr. 5, 2002

(65) Prior Publication Data

US 2003/0191057 A1 Oct. 9, 2003

(51) Int. Cl.[7] .................. A61K 38/08; A61K 38/10; A61K 38/16; C07K 7/06; C07K 7/08
(52) U.S. Cl. .................. 514/2; 514/7; 514/12; 514/13; 514/14; 514/15; 530/300; 530/324; 530/325; 530/326; 530/327; 530/328; 530/345
(58) Field of Search .................. 530/300, 324, 530/325, 326, 327, 328, 345; 436/86, 87; 514/2, 7, 12, 13, 14, 15

(56) References Cited

U.S. PATENT DOCUMENTS

| | | | |
|---|---|---|---|
| 3,767,040 A | 10/1973 | Tushaus | 428/352 |
| 4,155,913 A | 5/1979 | Hellerbach et al. | 546/276 |
| 4,643,988 A | 2/1987 | Segrest et al. | 514/12 |
| 5,358,934 A | * 10/1994 | Borovsky et al. | 514/17 |
| 5,721,138 A | 2/1998 | Lawn | 435/325 |
| 5,733,549 A | 3/1998 | Yamada et al. | 424/185.1 |
| 5,733,879 A | 3/1998 | Rosseneu et al. | 514/13 |
| 5,814,467 A | 9/1998 | Curtiss et al. | 435/7.9 |
| 5,854,238 A | 12/1998 | Kempen | 514/220 |
| 6,004,925 A | 12/1999 | Dasseux et al. | 514/2 |
| 6,037,323 A | 3/2000 | Dasseux et al. | 514/12 |
| 6,046,166 A | 4/2000 | Dasseux et al. | 514/13 |
| 6,086,918 A | 7/2000 | Stern et al. | 424/474 |
| 6,265,377 B1 | 7/2001 | Dasseux et al. | 514/12 |
| 6,287,590 B1 | 9/2001 | Dasseux et al. | 424/450 |
| 6,329,341 B1 | 12/2001 | Dasseux et al. | 514/13 |
| 6,376,464 B1 | 4/2002 | Dasseux et al. | 514/12 |
| 6,455,088 B1 | 9/2002 | Dasseux et al. | 426/450 |
| 6,518,412 B1 | 2/2003 | Dasseux et al. | 536/23.1 |
| 6,573,239 B1 | 6/2003 | Dasseux et al. | 514/12 |
| 6,602,854 B1 | 8/2003 | Dasseux et al. | 514/13 |
| 6,630,450 B1 | 10/2003 | Dasseux et al. | 514/13 |
| 6,716,816 B1 | 4/2004 | Dasseux et al. | 514/13 |
| 6,734,169 B2 | 5/2004 | Dasseux et al. | 514/12 |
| 6,753,313 B1 | 6/2004 | Dasseux et al. | 514/12 |
| 2001/0005714 A1 | 6/2001 | Boffelli et al. | 514/21 |
| 2003/0045460 A1 | 3/2003 | Fogelman et al. | 514/12 |

FOREIGN PATENT DOCUMENTS

| | | |
|---|---|---|
| EP | 1186299 A1 | 2/2002 |
| IN | 185761 | 4/2001 |
| WO | WO 91/05043 A1 * | 4/1991 |
| WO | WO 97/36927 | 10/1997 |
| WO | WO 97/36927 A1 | 10/1997 |
| WO | WO 99/47566 A1 | 9/1999 |
| WO | WO 00/34469 A1 * | 6/2000 |
| WO | WO 02/22161 A2 * | 3/2002 |

OTHER PUBLICATIONS

Aravinda, S., Shamala, N., Das, C., Sriranjini, A., Karle, I. And Balaram, P. Aromatic–Aromatic Interactions in Crystal Structures of Helical Peptide Scaffolds Containing Projecting Phenylalinine Residues, J.Am. Chem Soc. 2003; 125:5308–5315.

(Continued)

*Primary Examiner*—Jeffrey Edwin Russel
(74) *Attorney, Agent, or Firm*—Quine I. P. Law Group, P.C.; Tom Hunter

(57) ABSTRACT

This invention provides novel peptides that ameliorate one or more symptoms of atherosclerosis and/or other pathologies characterized by an inflammatory response. In certain embodiment, the peptides resemble a G* amphipathic helix of apolipoprotein J. The peptides are highly stable and readily administered via an oral route.

102 Claims, 7 Drawing Sheets

OTHER PUBLICATIONS

Ashby D, Gamble J, Vadas M, Fidge N, Siggins S, Rye K, Barter PJ. Lack of effect of serum amyloid A (SAA) on the ability of high-density lipoproteins to inhibit endothelial cell adhesion molecule expression. *Atherosclerosis.* 2001;154:113–121.

Ashby DT, Rye K-A, Clay MA., Vadas MA, Gamble J, Barter PJ. Factors influencing the ability of HDL to inhibit expression of vascular cell adhesion molecule-1 in endothelial cells. *Arteriosclerosis, Thrombosis and Vascular Biology,* 1998,18:1450–1455.

Baker PW, Rye K-A, Gamble JR, Vadas MA, Barter PJ. Ability of reconstituted high density lipoproteins to inhibit cytokine–induced expression of vascular cell adhesion molecule–1 in human umbilical cell endothelial cells. *Journal of Lipid Research,* 1999, 40:345–353.

Baker PW, Rye KA, Gamble JR, Vadas MA, Barter PJ. Phospholipid composition of reconstituted high density lipoproteins influences their ability to inhibit endothelial cell adhesion molecule expression. *J Lipid Res* 2000;41:1261–1267.

Barter PJ, Baker PW, Rye K-A.. Effect of high–density lipoproteins on the expression of adhesion molecules in endothelial cells. *Current Opinion in Lipidology,* 2002, 13:285–288.

Barter PJ, Rye K-A. High density lipoproteins and coronary heart disease. *Atherosclerosis,* 1996, 121:1–12.

Blankenberg S, Rupprecht HJ, Bickel C, Peetz D, Hafner G, Tiret L, Meyer J. Circulating cell adhesion molecules and death in patients with coronary artery disease. *Circulation* 2001;104:1336–1342.

Bourdillon MC, Poston RN, Covacho C, Chignier E, Bricca G, McGregor JL. ICAM–1 deficiency reduces atherosclerotic lesions in double–knockout mice (ApoE(–/–)/ICAM–1(–/–)) fed a fat or a chow diet. *Arterioscler Thromb Vasc Biol* 2000;20:2630–2635.

Bowry VW, Stanley KK, Stocker R. High density lipoprotein is the major carrier of lipid hydroperoxides in human blood plasma from fasting donors. *Proc Natl Acad Sci U S A.* 1992;89:10316–10320.

Burger D, Dayer J–M. High–density lipoprotein–associated apolipoprotein A–I: the missing link between infection and chronic inflammation? *Autoimmunity Reviews* 2002;1:111–117.

Calabresi L, Franceschini G, Sirtori CR, De Palma A, Saresella M, Ferrante P, Taramelli D. Inhibition of VCAM–1 expression in endothelial cells by reconstituted high density lipoproteins. *Biochem Biophys Res Commun.* 1997;238:61–65.

Calabresi L, Gomaraschi M, Villa B, Omoboni L, Dmitrieff C, Franceschini G. Elevated cellular adhesion molecules in subjects with low HDL–cholesterol. *Arterioscler Thromb Vasc Biol* 2002;22:656–661.

Carlos TM, Schwartz BR, Kovach NL, Yee E, Rosa M, Osborn L, Chi–Rosso G, Newman B, Lobb R, Rosso M, et al. Vascular cell adhesion molecule–1 mediates lymphocyte adherence to cytokine–activated cultured human endothelial cells. *Blood* 1990;76:965–970.

Carr AC, McCall MR, Frei B. Oxidation of LDL by myeloperoxidase and reactive nitrogen species oxidation of LDL by myeloperoxidase and reactive nitrogen species. *Arterioscler Thromb Vasc Biol.* 2000;20:1716–1723.

Castelli WP, Garrison RJ, Wilson PW, Abbott RD, Kalousdian S, Kannel WB. Incidence of coronary heart disease and lipoprotein cholesterol levels. The Framingham study. *JAMA* 1986;256:2835–2838.

Chiesa G, Monteggia E, Marchesi M, Lorenzon P, Laucello M, Lorusso V, Di Mario C, Karvouni E, Newton RS, Bisgaier CL, Franceschini G, Sirtori CR. Recombinant apolipoprotein A–I(Milano) infusion into rabbit carotid artery rapidly removes lipid from fatty streaks. *Circ Res.* 2002;90:974–980.

Christison J, Karjalainen A, Brauman J, Bygrave F, Stocker R. Rapid reduction and removal of HDL– but not LDL–associated cholesteryl ester hydroperoxides by rat liver perfused in situ. *Biochem J.* 1996;314:739–742.

Clay MA, Pyle DH, Rye K–A, Vadas MA, Gamble JR, Barter PJ. Time sequence of the inhibition of endothelial adhesion molecule expression by reconstituted high density lipoproteins. *Atherosclerosis,* 2001,157:23–29.

Cockerill GW, Huehns TY, Weerasinghe A, Stocker C, Lerch PG, Miller NE, Haskard DO. Elevation of plasma high–density lipoprotein concentration reduces interleukin–1–induced expression of E–selectin in an in vivo model of acute inflammation. *rculation* 2001;103:108–112.

Cockerill GW, Rye KA, Gamble JR, Vadas MA, Barter PJ. High–density lipoproteins inhibit cytokine–induced expression of endothelial cell adhesion molecules. *Arterioscler Thromb Vasc Biol.* 1995;15:1987–1994.

Cockerill GW, Saklatvala J, Ridley SH, Yarwood H, Miller NE, Oral B, Nithyanathan S, Taylor G, Haskard DO. High–density lipoproteins differentially modulate cytokine–induced expression of E–selectin and cyclooxygenase–2. *Arterioscler Thromb Vasc Biol.* 1999;19:910–917.

Cybulsky MI, Iiyama K, Li H, et al. A major role for VCAM–1, but not ICAM–1, in early atherosclerosis. *Journal of Clinical Investigation* 2001;107:1255–1262.

Cyrus T, Pratico D, Zhao L, Witztum JL, Rader DJ, Rokach J, FitzGerald GA, Funk CD. Absence of 12/15–lipoxygenase expression decreases lipid peroxidation and atherogenesis in apolipoprotein E–dificient mice. *Circulation.* 2001;103:2277–2282.

Dansky HM, Barlow CB, Lominska C, Sikes JL, Kao C, Weinsaft J, Cybulsky MI, Smith JD. Adhesion of monocytes to arterial endothelium and initiation of atherosclerosis are critically dependent on vascular cell adhesion molecule–1 gene dosage. *Arterioscler Thromb Vasc Biol* 2001;21:1662–1667.

Dansky HM, Charlton SA, Barlow CB, Tamminen M, Smith JD, Frank JS, Breslow JL. Apo A–I inhibits foam cell formation in Apo E–deficient mice after monocyte adherence to endothelium. *J Clin Invest.* 1999;104:31–39.

Davenport P, Tipping PG. The role of interleukin–4 and interleukin–12 in the progression of atherosclerosis in apolipoprotein E–deficient mice. *Am J Pathol* 2003;163:1117–1125.

Davies MJ, Gordon JL, Gearing AJ, Pigott R, Woolf N, Katz D, Kyriakopoulos A. The expression of the adhesion molecules ICAM–1, VCAM–1, PECAM, and Eselectin in human atherosclerosis. *J Pathol* 1993;171:223–229.

De Caterina R, Bernini W, Carluccio MA, Liao JK, Libby P. Structural requirements for inhibition of cytokine–induced endothelial activation by unsaturated fatty acids. *J. Lipid Res.* 1998;39:1062–1070.

Dimayuga P, Zhu J, Oguchi S, Chyu KY, Xu XO, Yano J, Shah PK, Nilsson J, Cercek B. Reconstituted HDL containing human apolipoprotein A–1 reduces VCAM–1 expression and neointima formation following periadventitial cuffinduced carotid injury in apoE null mice. *Biochem Biophys Res Commun.* 1999;264:465–468.

Epand RM, Stafford A, Leon B, Lock PE, Tytler EM, Segrest JP, Anantharamaiah GM. HDL and apolipoprotein A–I protect erythrocytes against the generation of procoagulant activity. *Arterioscler. Thromb.* 1994;14:1775–1783.

Fleisher LN, Tall AR, Witte LD, Miller RW, Cannon PJ. Stimulation of arterial endothelial cell prostacyclin synthesis by high density lipoproteins. *J. Biol. Chem.* 1982;257:6653–6655.

Fogelman AM, Shechter I, Seager J, Hokom M, Child JS, Edwards PA. Malondialdehyde alteration of low density lipoproteins leads to cholesteryl ester accumulation in human monocyte–macrophages. *Proc Natl Acad Sci U S A.* 1980;77:2214–2218.

Fogelman AM. When good cholesterol goes bad. Nat Med 2004;10:902–903.

Forte TM, Subbanagounder G, Berliner JA, Blanche PJ, Clermont AO, Jia Z, Oda MN, Krauss RM, Bielicki JK. Altered activities of anti–atherogenic enzymes LCAT, paraoxonase, and platelet–activating factor acetylhydrolase in atherosclerosis–susceptible mice. *J. Lipid Res.* 2002;43:477–485.

Gabay C, Kushner I. Acute–phase proteins and other systemic responses to inflammation. *N. Engl. J. Med.* 1999; 340: 448–454.

Garner B, Waldeck AR, Witting PK, Rye KA, Stocker R. Oxidation of high density lipoproteins. II. Evidence for direct reduction of lipid hydroperoxides by methionine residures of apolipoproteins AI and AII. *J Biol Chem* 1998;273:6088–6095.

Garner B, Witting PK, Waldeck AR, Christison JK, Raftery M, Stocker R. Oxidation of high density lipoproteins. I. Formation of methionine sulfoxide in apolipoproteins AI and AII is an early event that accompanies lipid peroxidation and can be enhanced by alpha–tocopherol. *J Biol Chem* 1998;273:6080–6087.

Gaut JP, Byun J, Tran HD, Lauber WM, Carroll JA, Hotchkiss RS, Belaaouaj A, Heinecke JW. Myeloperoxidase produces nitrating oxidants in vivo. *J Clin Invest* 2002;109:1311–1319.

George J, Afek A, Shaish A, Levkovitz H, Bloom N, Cyrus T, Zhao L, Funk CD, Sigal E, Harats D. 12/15–lipoxygenase gene disruption attenuates atherogenesis in LDL receptor–deficient mice. *Circulation.* 2001;104:1646– 1650.

Gordon T, Castelli WP, Hjortland MC, et al. High density lipoprotein as a protective factor against coronary heart disease. *Am. J. Med.*1977;62: 707–714.

Harats D, Shaish A, George J, Mulkins M, Kurihara H, Levkovitz H, Sigal E. Overexpression of 15–lipoxygenase in vascular endothelium accelerates early atherosclerosis in LDL receptor–deficient mice. *Arterioscler Thromb Vasc Biol.* 2000;20:2100–2105.

Henricksen T, Mahoney EM, Steinberg D. Enhanced macrophage degradation of low density lipoprotein previously incubated with cultured endothelial cells: recognition by receptor for acetylated low density lipoproteins. *Proc Natl Acad Sci U S A.* 1981;78:6499–6503.

Hessler JR, Robertson AL, Chisolm GM. LDL–induced cytotoxicity and its inhibition by HDL in human vascular smooth muscle and endothelial cells in culture. *Atherosclerosis* 1979; 32:213–229.

Hwang SJ, Ballantyne CM, Sharrett AR, Smith LC, Davis CE, Gotto AM Jr, Boerwinkle E. Circulating adhesion molecules VCAM–1, ICAM–1, and E–selectin in carotid atherosclerosis and incident coronary heart disease cases. The atherosclerosis risk in communities (ARIC) study. *Circulation* 1997;96:4219–4225.

Jin W, Millar JS, Broedl U, et al. Inhibition of endothelial lipase causes increased HDL cholesterol levels in vivo. *J Clin Invest* 2003;111:357–362.

Karle, I., Gopi, H., and Balaram, P. Crystal structure of hydrophobic 19–residue peptide helix containing three centrally located D amino acids PNAS 2003;100:24:13946–13951.

Karle, I, Prasad, S. and Balaram, P. A combined extented and helical backbone for Boc–(Ala–Leu–Ac7C)2–OME, Peptides Res. 2004; 63:174–180.

Ko Y, Haring R, Stibler H, Wieczorek AJ, Vetter H, Sachinidis A. Highdensity lipoprotein reduces epidermal growth factor–induced DNA synthesis in vascular smooth muscle cells. *Atherosclerosis* 1993;99: 253–259.

Kume N, Cybulsky MI, Gimbrone Jr MA. Lysophosphatidylcholine, a component of atherogenic lipoproteins, induces mononuclear leukocyte adhesion molecules in cultured human and rabbit arterial endothelial cells. *Journal of Clinical Investigation* 1992;90:1138–1144.

Lawrence MB, Springer TA. Leukocytes roll on a selectin at physiologic flow rates: distinction from and prerequisite for adhesion through integrins. *Cell* 1991;65:859–873.

Lee SH, Oe T, Blair IA. Vitamin C–induced decomposition of lipid hydroperoxides to endogenous genotoxins. *Science* 2001;292:2083–2086.

Levine DM, Parker TS, Donnelly TM, Walsh A, Rubin AL. In vivo protection against endotoxin by plasma high density lipoprotein. *Proc. Natl. Acad. Sci.* USA 1993:90 : 12040–12044.

Li H, Cybulsky MI, Gimbrone MA, Jr., Libby P. An atherogenic diet rapidly induces VCAM–1, a cytokine–regulatable mononuclear leukocyte adhesion molecule, in rabbit aortic endothelium. *Arteriosclerosis and Thrombosis* 1993;13:197–204.

Libby P, Ridker PM, Maseri A. Inflammation and atherosclerosis. *Circulation* 2002;105:1135–1143.

Mehrabian M, Allayee H, Wong J, Shi W, Wang XP, Shaposhnik Z, Funk CD, Lusis AJ, Shih W. Identification of 5–lipoxygenase as a major gene contributing to atherosclerosis susceptibility in mice. *Circ Res.* 2002;91:120–126.

Murugesan G, Sa G, Fox PL. High–density lipoprotein stimulates endothelial cell movement by a mechanism distinct from basic fibroblast growth factor. *Circ. Res.* 1994:74: 1149–1156.

Nanjee MN, Doran JE, Lerch PG, Miller NE. Acute effects of intravenous infusion of apoA–I/phosphosphatidycholine discs on plasma lipoproteins in humans.. *Arterioscler Thromb Vasc Biol.* 1999;19:979–989.

Nanjee MN, Cooke CJ, Garvin R, et al. Intravenous apoA–I/lecithin discs increase pre–b–HDL concentration in tissue fluid and stimulate reverse cholesterol transport in humans. *J Lipid Res* 2001;42:1586–1593.

Navab M, Anantharamaiah GM, Reddy ST, et al. The oxidation hypothesis of atherogenesis: the role of oxidized phospholipids and HDL. *J. Lipid Res.* 2004; 45: 993–1007.

Navab M, Anantharamaiah GM, Reddy ST, et al. Oral D–4F causes formation of pre □ high–density lipoprotein and improves high–density lipoprotein–mediated cholesterol efflux and reverse cholesterol transport from macrophages in apoE–null mice. *Circulation* 2004; 109:r120–r125.

Navab M, Berliner JA, Subbanagounder G, Hama S, Lusis AJ, Castellani LW, Reddy S, Shih D, Shi W, Watson AD, Van Lenten BJ, Vora D, Fogelman AM. HDL and the inflammatory response induced by LDL–derived oxidized phospholipids. *Arterioscler Thromb Vasc Biol* 2001;21:481–488.

Navab M, Hama S, Hough G et al. Oral synthetic phospholipids (DMPC) raises high–density lipoprotein cholesterol levels, improves high–density lipoprotein function, and markedly reduces atherosclerosis in apolipoprotein E–null mice. *Circulation* 2003;108:1735–1739.

Navab M, Hama SY, Hough GP, et al. A cell–free assay for detecting HDL that is dysfunctional in preventing the formation of or inactivating oxidized phospholipids. *J Lipid Res* 2001;42:1308–1317.

Navab M, Hama–Levy, S, Van Lenten BJ, et al. Mildly oxidized LDL induces an increased apolipoprotein J/paraoxonase ratio. *J. Clin. Invest.* 1997; 99: 2005–2019.

Navab M, Imes SS, Hama SY, Hough GP, Ross LA, Bork RW, Valente AJ, Berliner JA, Drinkwater DC, Laks H,, et al. Monocyte transmigration induced by modification of low density lipoprotein in cocultures of human aortic wall cells is due to induction of monocyte chemotactic protein 1 synthesis and is abolished by high density lipoprotein. *Journal of Clinical Investigation* 1991;88:2039–2046.

Nievelstein PF, Fogelman AM, Mottino G, Frank JS. Lipid accumalation in rabbit aortic intima two hours after bolus infusion of low density lipoprotein: A deep–etch and immuno–localization study of ultra–rapidly frozen tissue. *Arteriosclerosis and Thrombosis* 1991;11:1795–1805.

Lumsden AB, Chen C, Hughes JD, Kelly AB, Hanson SR, Harker LA. Anti– VLA–4 antibody reduces intimal hyperplasia in the endarterectomized carotid artery in nonhuman primates. *J Vasc Surg* 1997;26:87–93.

Mach F, Schonbeck U, Sukhova GK, Atkinson E, Libby P. Reduction of atherosclerosis in mice by inhibition of CD40 signalling. *Nature* 1998;394:200– 203.

O'Brien KD, McDonald TO, Chait A, Allen MD, Alpers CE. Neovascular expression of E–selectin, intercellular adhesion molecule–1, and vascular cell adhesion molecule–1 in human atherosclerosis and their relation to intimal leukocyte content. *Circulation* 1996;93:672–82.

O'Connell BJ, Genest J Jr. High–density lipoproteins and endothelial function. *Circulation* 2001;104:1978–1983.

Oguchi S, Dimayuga P, Zhu J, Chyu KY, Yano J, Shah PK, Nilsson J, Cercek B. Monoclonal antibody against vascular cell adhesion molecule–1 inhibits neointimal formation after periadvential carotid artery injury in genetically hypercholesterolemic mice. *Arteriosclr Thromb Vasc Biol* 2000;20:1729–1736.

Papo N, Oren Z, Pag U, et al. The consequence of sequence alteration of an amphipathic α–helical antimicrobial peptide and its diastereomers. *J. Biol. Chem.* 2002;277(37):33913–33921.

Parthasarathy S, Santanam N. Mechanisms of oxidation antiodixants, and atherosclerosis. *Curr Opin Lipidol* 1994;5:371–375.

Pasceri V, Cheng JS, Willerson JT, Yeh ET, Chang J. Modulation of Creative protein–mediated monocyte chemoattractant protein–1 induction in human endothelial cells by anti–atherosclerosis drugs. *Circulation.* 2001;103:2531–2534.

Pasceri V, Willerson JT, Yeh ET. Direct proinflammatory effect of C–reactive protein on human endothelial cells. *Circulation.* 2000;102:2165–2168.

Ou J, Geiger T, Zhijun O, et al. AP–4F, antennapedia peptide linked to an amphipathic α helical peptide, increases the efficiency of lipofectamine–mediated gene transfection in endothelial cells. *Biochem Biophys Res Commun* 2003;305:605–610.

Ou J, Ou Z, Jones DW, et al. L–4F, an apolipoprotein A–I mimetic, dramatically improves vasodilation in hypercholesterolemic and sickle cell disease. *Circulation* 2003;107:2337–2341.

Ou Z, Ou J, Ackerman AW et al. L–4F, an apolipoprotein A–I mimetic, restores nitric oxide and superoxide anion balance in low–density lipoprotein–treated endothelial cells. *Circulation* 2003;107:1520–1524.

Ranganathan, D, Kurur, S, Kunwar, A, Sarma, A, Vairamani, M, Karle, I. Channel–forming, self–assembling, bishelical amphiphilic peptides: design, synthesis and crystal structure of PY(Aibn)21 n=2, 3, 4. J. Peptide Res. 2000 56:416–426.

Reape TJ, Groot PH. Chemokines and atherosclerosis. *Atherosclerosis* 1999;147:213–225.

Reddy ST, Wadleigh DJ, Grijalva V, Ng C, Hama S, Gangopadhyay A, Shih DM, Lusis AJ, Navab M, Fogelman AM. Human paraoxonase–3 is an HDLassociated enzyme with biological activity similar to paraoxonase–1 protein but is not regulated by oxidized lipids. *Arterioscler Thromb Vasc Biol* 2001;21:542–547.

Reddy ST, Nguyen JT, Grijalva V, et al. Potential role for mitogen–activated protein kinase phosphatase–1 in the development of atherosclerotic lesions in mouse models. *Arterioscler Thromb Vasc Biol* 2004;24:1676–1681.

Ridker PM. On evolutionary biology, inflammation, infection, and the causes of atherosclerosis. *Circulation* 2002;105:2–4.

Rong JX, Li J, Reis ED, Choudhury RP, Dansky HM, Elmalem VI, Fallon JT, Breslow JL, Fisher EA. Elevating high–density lipoprotein cholesterol in apolipoprotein E–deficient mice remodels advanced atherosclerotic lesions by decreasing macrophage and increasing smooth muscle cell content. *Circulation* 2001;104:2447–2452.

Sattler W, Stocker R. Greater selective uptake by Hep G2 cells of highdensity lipoprotein cholesteryl ester hydroperoxides than of unoxidized chelesteryl esters. *Biochem J.* 1993;294:771–778.

Shah PK, Nilsson J, Kaul S. Effects of recombinant apolipoprotein A–I(Milano) on aortic atherosclerosis in apolipoprotein E–deficient mice. *Circulation,* 1998:97(8):780–785.

Shah PK, Yano J, Reyes O, Chyu KY, Kaul S, Bisgaier CL, Drake S, Cercek B. High–dose recombinant apolipoproteins A–IMilano mobilizes tissue cholesterol and rapidly reduces plaque lipid and macrophage content in apolipoprotein Edeficient mice: potential implications for acute plaque stabilization. *Circulation.* 2001;103:3047–3050.

Shih D.M., Xia Y–R., Wang X–P., Miller E., Castellani L.W., Subbanagounder G., Cheroutre H., Faull K., Berliner J.A., Witztum J.L., Lusis A.J. Combined serum paraoxonase/apolipoprotein E knockout mice exhibit increased lipoprotein oxidation and atherosclerosis. *J. Biol. Chem.,* 2000;275:17527–17535.

Shih PT, Elices MJ, Fang ZT, Ugarova TP, Strahl D, Territo MC, Frank JS, Kovach NL, Cabanas C, Berliner JA, Vora DK. Minimally modified low–density lipoprotein induces monocyte adhesion to endothelial connecting segment–1 by activating beta integrin. *J Clin Invest* 1999;103:613–625.

Shishehbor MH, Aviles RJ, Brennan ML, Fu X, Goormastic M, Pearce GL, Gokce N, Keaney JF Jr, Penn MS, Sprecher DL, Vita JA, Hazen SL. Association of nitrotyrosine levels with cardiovascular disease and modulation by statin therapy. *JAMA* 2003:289:1675–1680.

Singh IP, Baron S. Innate defences against viremia. *Rev Med Virol* 2000;10:395–403.

Sorescu D, Szocs K, Griendling KK. NAD(P)H oxidases and their relevance to atherosclerosis. *Trends Cardiovas Med* 2001;11:124–131.

Spieker LE, Sudano I, Hurlimann D, Lerch PG, Lang MG, Binggeli C, Corti R, Ruschitzka F, Luscher TF, Noll G. High–density lipoprotein restores endothelial function in hypercholesterolemic men. *Circulation.* 2002;105:1399–1402.

Springer TA. Adhesion receptors of the immune system. *Nature* 1990;346:425–434.

Stannard AK, Khan S, Graham A, Owen JS, Allen SP. Inability of plasma high–density lipoproteins to inhibit cell adhesion molecule expression in human coronary artery endothelial cells. *Atherosclerosis* 2001;154:31–38.

Sugatani J, Miwa M, Komiyama Y, Ito S. High–density lipoprotein inhibits the synthesis of platelet–activating factor in human vascular endothelial cells. *J. Lipid Mediators Cell Signal.* 1996:13:73–88.

Tward A, Xia YR, Wang XP, Shi YS, Park C, Castellani LW, Lusis AJ, Shih DM. Decreased atherosclerotic lesion formation in human serum paraoxonase transgenic mice. *Circulation* 2002;106:484–490.

Van Lenten BJ, Hama SY, de Beer FC, Stafforini DM, McIntyre TM, Prescott SM, La Du BN, Fogelman AM, Navab M. Anti–inflammatory HDL becomes proinflammatory during the acute phase response. Loss of protective effect of HDL against LDL oxidation in aortic wall cell cocultures. *J Clin Invest* 1995;96:2758–2767.

Van Lenten BJ, Wagner AC, Nayak DP, Hama S, Navab M, Fogelman AM. High–density lipoprotein loses its anti–inflammatory properties during acute influenza A infection. Circulation 2001;103:2283–2288.

Van Lenten BJ, Wagner AC, Anantharamaiah GM, Garber DW, Fishbein MC, Adhikary L, Nayak DP, Hama S, Navab M, Fogelman AM. Influenza infection promotes macrophage traffic into arteries of mice that is prevented by D–4F, an apolipoprotein A–I mimetic peptide. *Circulation* 2002; 106:1127–1132.

Venugopal SK, Devaraj S, Yuhanna I, Shaul P, Jialal I. Demonstration that C–reactive protein decreases eNOS expression and bioactivity in human aortic endothelial cells. *Circulation.* 2002;106:1439–1441.

Walpola PL, Gotlieb AI, Cybulsky MI, Langille BL. Expression of ICAM–1 and VCAM–1 and monocyte adherence in arteries exposed to altered shear stress. *Arterioscler Thromb Vasc Biol* 1995;15:2–10.

Watson AD, Navab M, Hama SY, Sevanian A, Prescott SM, Stafforini DM, McIntyre TM, Du BN, Fogelman AM, Berliner JA. Effect of platelet activating factor–acetylhydrolase on the formation and action of minimally oxidized–low density lipoprotein. *J Clin Invest* 1995;95:774–782.

Watson AD, Berliner JA, Hama SY, et al. Protective effect of high density lipoprotein associated paraoxonase. Inhibition of the biological activity of minimally oxidized low density lipoprotein. *J Clin Invest* 1995;96:2882–2891.

Xia P, Vadas MA, Rye KA, Barter PJ, Gamble JR High density lipoproteins (HDL) interrupt the sphingosine kinase signaling pathway. A possible mechanism for protection against atherosclerosis by HDL. *J Biol Chem.* 1999;274:33143–33147.

Yamashita S, Maruyama T, Hirano K, et al. Molecular mechanisms, lipoprotein abnormalities and atherogenicity of hyperalphalipoproteinemia. *Atherosclerosis* 2000;152:271–285.

Yan D, Navab M, Bruce C et al. PLTP deficiency improves the anti–inflammatory properties of HDL and reduces the ability of LDL to induce monocyte chemotactic activity. *J Lipid Res* 2004;45:1852–1858.

Yui Y, Aoyama T, Morishita H, Takahashi M, Takatsu Y, Kawai C. Serum prostacyclin stabilizing factor is identical to apolipoprotein A–I (Apo A–I). A novel function of Apo A–I. *J. Clin. Invest.* 1988;82: 803–807.

Zeiher AM, Schachinger V. Hohnloser SH, et al. Coronary atherosclerotic wall thickening and vascular reactivity in humans. Elevated high–density lipoprotein levels ameliorate abnormal vasoconstriction in early atherosclerosis. *Circulation* 1994;89:2525–2532.

Zhang R, Brennan ML, Shen Z, MacPherson JC, Schmitt D, Molenda CE, Hazen SL. Myeloperoxidase functions as a major enzymatic catalyst for initiation of lipid peroxidation at sites of inflammation. *J Biol Chem* 2002;277:46116–46122.

Zhang WJ, Stocker R, McCall MR, Forte TM, Frei B. Lack of inhibitory effect of HDL on TNFalpha–induced adhesion molecule expression in human aortic endothelial cells. *Ahterosclerosis* 2002;165:241–249.

Zhao L, Cuff CA, Moss e, Wille U, Cyrus T, Klein EA, Pratico D, Rader DJ, Hunter CA, Pure E, Funk CD. Selective interleukin–12 synthesis defect in 12/15–lipoxygenase deficient macrophages associated with reduced ahterosclerosis in a ouse model of familial hypercholesterolemia. *J Biol Chem* 2002;277:35350–35356.

Anantharamaiah et al. (1993) Pp. 109 In: The Amphipathic Helix, (Ed R.M. Epand.CRC press, Ann Arbor Mi).

Bailey et al. (2001) Biochemistry; 40: 11828–11840.

Clero et al. (1999) Biochem J; 344: 375–383.

Dota et al. (1999) Exp Eye Res; 69: 705–708.

Fleming et al. (1999) J Molecular Endocrinology; 23:199–208.

Gelissen et al. (1998) Biochem J; 331: 231–237.

Collard et al. (1987) Biochemistry; 26:3297–3303.

Hammad et al. (1997) J Biol Chem; 272: 18644–18649.

Han et al. (2001) Nature Medicine;7 338–343.

Hasan et al. (2000) Hum Pathol; 31: 691–697.

Hochgrebe et al. (1999) Experimental Cell Research;249: 13–21.

Hough et al.(2001) Cancer Res; 61: 3869–3876.

Ishikawa et al. (1998) Arterioscler Thromb Vasc Biol: 18: 665–672.

Ishikawa et al. (2001) Atherosclerosis; 158: 215–225.

Jenne et al. (1989) *Proc Natl Acad Sci* USA.; 86: 7123–7127.
Khan et al. (2000) Pathology; 258–261.
Kissinger et al. (1982) Biol Reprod 1982; 27:233–240.
Landes (1995) Pp. 1–12 In: Clusterin: Role in Vertebrate Development, Function, and Adaptation (Harmony JAK Ed.) pp 1–12, R.G.
Mackness et al. (1997) Arterioscler Thromb Vasc Biol; 17: 1233–1238.
McLaughlinet al. (2000) J Clin Invest; 106:1105–1113.
Mitsuhashi et al. (1997) J Clin Invest; 100: 847–854.
Morrissey et al. (2001) J Biochem Biophys Methods;48: 13–21.
Navab et al. (1997) J Clin Invest; 99:2005–2019.
Navab et al. (2000) J Lipid Res; 41:1495–1508.
Navab et al. (2000) J Lipid Research;41:1481–1494.
Navab et al. (2001) Arterioscler Thromb Vasc Biol. 2001;21:481–488.
Navab et al. (2001) Arterioscler Thromb Vasc Biol; 21:1451–1457.
Navab et al. (2002) Circulation; 105:290–292.
Newkirk et al. (1999) J Rheumatol; 26: 597–603.
Nishida et al. (1999) *Br J Ophthalmol;* 83: 1178–1182).
Redondo et al. (2000) Am J Pathol; 157:393–399.
Segrest et al. (1990). Proteins:Structure, Function and Genetics; 8:103–117 Erratum (1991) Proteins:Structure, Function and Genetics 1991; 9:79.
Silkensen et al. (1999) Pept Res; 54: 449–457.
Steinberget al. (1997) Clin Cancer Res;3: 1707–1711.
Van Lenten et al. (2001) Circulation;103: 2283–2288.
Van Lenten et al. (2001) J Biol Chem;276: 1923–1929.
Wehrli et al. (2001) Nature Medicine; 7: 977–978.
Wellman et al. (2000) Blood; 96: 398–404.
Wong et al.(2000) Vision; 6: 184–191.
Xu et al.(2000) J Biol Chem; 275: 31770–3177.
Wellmann et al. (2000) "Detection of differntially expressed genes in lymphomas using cDNA arrays: identification of clusterin as a new diagnostic marker for anaplastic large-cell lymphomas." Blood; 96: 398–404.
Wilson et al. (1988) "High Density Lipoprotein Cholesterol and mortality: The Framingham Heart Study." *Arteriosclerosis* 8: 737–741.
Wong et al.(2000) "Clusterin protein diversity in the primate eye." Mol. Vision; 6: 184–191.
Xu et al. (2000) "Isolation and characterization of apolipoproteins from murine microglia. Identification of a low density lipoprotein–like apolipoprotein J–rich but E–poor spherical particle" J Biol Chem; 275: 31770–3177.
Yancey et al. (1995) "Efflux of Cellular Cholesterol and Phospholipid to Lipid–free Apolipoproteins and Class A Amphipathic Peptides." *Biochemistry,* 34: 7955–7965.
PCT Search Report for PCT/US03/09988, mailed Oct. 21, 2003.
Anantharamaiah (1986) "Synthetic Peptide Analogs of Appolipoproteins." *Methods in Enzymology* 128:627–647.
Anantharamaiah and Garber (1996) "Chromatographic Methods for Quantitation of Apolipoprotein A–I." *Meth. Enzymol.* 263: 267–282.
Anantharamaiah et al. (1985) "Studies of Synthetic Peptide of the Amphipathic Helix." *The Journal of Biological Chemistry* 260:10248–10255.

Anantharamaiah et al. (1990) "Use of Synthetic Peptide Analogues to Localize Lecithin: Cholesterol Acyltransferase Activating Domain in Apolipoprotein A–I." *Arteriosclerosis* 10:95–105.
Anantharamaiah et al. (1993) "An Atlas of the Amphipathic Helical Domains of Human Exchangeable Plasma Apolipoproteins." Chapter 6:109–142 In: *The Amphipathic Helix* (Epand, R. M., ed), CRC Press, Boca Raton, FL.
Armstrong et al. (1993) D amino acid levels in human physiological fluids, *Chirality,* 5: 375–378.
Atlas–White et al. (2000) "Localisation of clusterin in normal human sperm by immunogold electron microscopy." Patholody; 258–261.
Badimon et al. (1990) "Regression of Atherosclerotic Lesions by High Density Lipoprotein Plasma Fraction in the Cholesterol–fed Rabbit." *J. Clinical Investigation* 85:1234–1241.
Bailey et al. (2001) "Clusterin, a binding protein with a molten globule–like region." Biochemistry; 40: 11828–11840.
Bauer et al. (1982) "SMS 201–995: A Very Potent and Selective Octapeptide Analogue of Somatostatin with Prolonged Action" *Life Sciences* 31:1133–1140.
Boffelli et al. (1997) "Reconstitution and Further Characterization of the Cholesterol Transport Activity of the Small–Intestinal Brush Border Membrane" *Biochemistry* 36:10784–10792.
Boffelli et al. (1997) "The uptake of cholesterol at the small–intestinal brush border membrane is inhibited by apolipoproteins." FEBS Letters, 411: 7–11.
Borhani et al. (1999) "Crystal structure of truncated human apolipoprotein A–I suggests a lipid–bound conformation." *Proc. Natl. Acad. Sci. USA.* 94:12291–12296.
Brouillette and Anantharamaiah (1995) "Structural models of human apolipoprotein A–I." *Biochim. Biophys. Acta* 1256: 103–129.
Brouillette et al. (2001) "Structural Models of Human Apolipoprotein A–I: A Critical Analysis and Review" *Biochemica et Biophysica Acta* 1531:4–46.
Calero et al. (1999) "Functional and structural properties of lipid–associated apolipoprotein J (clusterin)." Biochem J; 344: 375–383.
Canadian Pharmacists Association, Starlix General Monograph. http://cpha.infinetcomm.com/content/hcp/tools/cps_cnp_updates/starlix.cfm (Dec. 10, 2002).
Chung et al. (1985) "Studies of Synthetic Peptide Analogs of the Amphipathic Helix." *J. Biol. Chem.* 60(18): 10256–10262.
Datta et al. (2001) Effects of Increasing Hydrophobicity on the Physical–Chemical and Biological Properties of a Class A Amphipathic Helical Peptide. *J Lipid Research* 42:1096–1104.
Davidson et al. (1994) "The Influence of Apolipoprotein Structure on the Efflux of Cellular Free Cholesterol to High Density Lipoprotein." *J. Biol. Chem.* 269(37): 22975–22982.
Diederich et al. (2001) "Apolipoprotein AI and $HDL_3$ Inhibit Spreading of Primary Human Monocytes through a Mechanism that Involves Cholesterol Depletion and Regulation of CD42." *Atherosclerosis* 159:313–324.
Dooley et al. (1994) "An All D–Amino Acid Opioid Peptide with Central Analgesic Activity from a Combinatorial Library" Science 2019–2022.

Dota et al. (1999) "Clusterin in human corneal endothelium and aqueous humor." Exp Eye Res; 69: 705–708.

Dunlop and Neidle (1997) "The Origion and Turnover of D–Serine in Brain." *Biochemical and Biophysical Research Communication* 235:26–30.

Ehara et al. (2001) "Elevated Levels of Oxidized Low Density Lipoprotein Show a Positive Relationship With the Severity of Acute Coronary Syndromes." *Circulation* 103:1955–1960.

Epand et al. (1987) "Studies Synthetic Peptide Analog of the Amphipathic Helix" *J. Biol. Chem.* 262(19): 9389–9396.

Field et al. (2001) "Gene expression of sterol regulatory element–binding proteins in hamster small intestine." *Journal of Lipid Research* 42:1–9.

Fielding and Fielding (1995) "Molecular physiology of reverse cholesterol transport." *J. Lipid Res.* 36: 211–228.

Fielding et al. (1972) "A Protein Cofactor of Lecithin: Cholester Acyltransferase." *Biochem. Biophys. Res. Comm.* 46(2):1493–1498.

Fleming et al. (1999) "Clusterin is expressed in the anterior and intermediate lobes, but not in the posterior pituitary of sheep." J Molecular Endocrinology; 23:199–208.

Fricker et al. (1995) "Enteral Absorption of Octreotide: Modulation of Intestinal Permeability by Distinct Carbohydrates" *The Journal of Pharmacology and Experimental Therapeutics* 274:826–832.

Fuessl et al. (1987) "Oral Absroption of the Somatostatin Analogue SMS 201–995: Theoretical and Practical Implications" *Clinical Science* 72: 255–257.

Garber et al. (1992) "Turnover of synthetic class A amphipathic peptide analogues of exchangeable apolipoproteins in rats. Correlation with physical properties." *Arteriosclerosis and Thrombosis,* 12(8): 886–894.

Garber et al. (1997) *Circulation* 96(8):I–490, Abstract 2744.

Garber et al. (1999) *Circulation* 100(18):I–538, Abstract 2838.

Garber et al. (2001) "A new synthetic class A amphipathic peptide analogue protects mice from diet–induced atherosclerosis." *Journal of Lipid Research* 42:545–552.

Gelissen et al. (1998) "Apolipoprotein J (clusterin) induces cholesterol export from macrophage–foam cells: a potential anti–atherogenic function?" Biochem J; 331: 231–237.

Glomset (1968) "The Plasma lecithin: cholesterol acytransferase reaction." *J. Lipid Res.* 9:155–167.

Gong et al. (1994) "Structural and functional properties of human and mouse apolipoprotein A–I." *Biochim. Biophys. Acta* 1213:335–342.

Collard et al. (1987) "Biosynthesis and molecular cloning of sulfated glycoprotein 2 secreted by rat Sertoli cells." Biochemistry; 26:3297–3303.

Gurfinkel et al. (2002) "Influenza Vaccine Pilot Study in Acute Coronary Syndromes and Planned Percutaneous Coronary Intervention. The FLU Vaccination Acute Coronary Syndromes (FLUVACS) Study" *Circulation* 105:2143–2147.

Hamase et al. (2001) "Determination of Free D–Proline and D–Leucine in the Brains of Mutant Mice Lacking D–Amino Acid Oxidase Activity" *Analytical Biochemistry* 298:253–258.

Hammad et al. (1997) "Interaction of apolipoprotein J–amyloid beta–peptide complex with low density lipoprotein receptor–related protein–2/megalin. A mechanism to prevent pathological accumulation of amyloid beta–peptide." J Biol Chem; 272: 18644–18649.

Han et al. (2001) "Clusterin contributes to caspase–3–independent brain injury following neonatal hypoxia–ischemia." Nature Medicine;7 338–343.

Hardy et al. (2001) "An Automated High–Performance Liquid Chromatography Procedure for the Quantitation of L– and D–Amino Acids by Means of Stepwise Precolumn Derivatization" Analytical Biochemistry 291:297–299.

Hasan et al. (2000) "Clusterin/apoJ expression during the development of hemangioma." Hum Pathol; 31: 691–697.

Hashimoto et al. (2000) "Improvement of intestinal absorption of peptides: absorption of B1–Phe monoglucosylated insulin to rat intestinal brush–border membrane vesicles." *J. Pharmaceutics & Therapeutics* 50(2):197–204.

Hauser et al. (1998) "Identification of a Receptor Mediating Absorption of Dietary Cholesterol in the Instestine" *Biochemistry* 178423–17850.

Hayry et al. "Stabile D–peptide analog of insulin–like growth factor–1 inhibits smooth muscle cell proliferation after carotid ballooning injury in the rat." *FASEB J.* 9(13):1336–1344 (1995).

Hochgrebe et al. (1999) "A reexamination of the role of clusterin as a complement regulator." Experimental Cell Research;249: 13–21.

Hough et al.(2001) "Coordinately up–regulated genes in ovarian cancer." Cancer Res; 61:3869–3876.

Hyka et al. (2001) "Apolipoprotein A–I Inhibits the Production of Interleukin–1beta and Tumor Necrosis Factor–alpha by Blocking Contact–Mediated Activation of Monocytes by T Lymphocytes." Blood 97:2381–2389.

Ishikawa et al. (1998) "Distribution and synthesis of apolipoprotein J in the atherosclerotic aorta." Arterioscler Thromb Vasc Biol: 18: 665–672.

Ishikawa et al. (2001) "Immunolocalization of apolipoproteins in aortic atherosclerosis in American youths and young adults: findings from the PDAY study." Atherosclerosis; 158: 215–225.

Jenne et al. (1989) "Molecular structure and functional characterization of a human complement cytolysis inhibitor found in blood and seminal plasma: identity to sulfated glycoprotein 2, a constituent of rat testis fluid." Proc Natl Acad Sci USA.; 86: 7123–7127.

Johnson et al. (1991) "Cholesterol transport between cells and high–density lipoproteins."*Biochim. Biophys. Acta.* 1085: 273–298.

Jonas (1991) "Lecithin–cholesterol acyltransferase in the metabolism of high–density lipoproteins." *Biochim. Biophys. Acta* 1084: 205–220.

Jonas (2000) Lecithin cholesterol acyltransferase. *Biochim. Biophys. Acta* 1529: 245–256.

Jones et al. (1992) "Computer Programs to Identify and Classify Amphipathic alpha Helical Domains" *Journal of Lipid Research* 33:287–296.

Kigasawa et al. (1995) "Inhibition of corneal ulceration by tetrapeptidyl hydroxamic acid." *Jap. J. Ophthamology* 39(1):35–42.

Kissinger et al. (1982) "Analysis of Sertoli cell–secreted proteins by two–dimensional gel electrophoresis." Biol Reprod 1982; 27:233–240.

Kriearr (1999) "Charting The Fate of the "Good Cholesterol": Identification and Characterization of the High–Density Lipoprotein Receptor Sr–Bi." *Ann Rev. Biochem.* 68: 523–558.

Kullman etal. (1999) "Evaluation of the Enantiomeric Composition of Amino Acids in Tobacco" *Chirality* 11:669–673.

Landes (1995) Pp. 1–12 In: Clusterin: Role in Vertebrate Development, Function, and Adaptation (Harmony JAK Ed.) pp 1–12, R.G.

Levi et al. (2000) "A retro–inverso minantibody with anti–HIV activity." *Aids Res. & Human Retruvirus* 16(1):59–65.

Lundin et al. (1986) "Absorption of Intragastrically Administered DDAVP in Conscious Dogs" *Life Sciences* 38:703–709.

Mackness et al. (1997) "Increased immunolocalization of paraoxonase, clusterin, and apolipoprotein A–I in the human artery wall with the progression of atherosclerosis." Arterioscler Thromb Vasc Biol; 17: 1233–1238.

Mackness et al. (2001) "Paraoxonase status in coronary heart disease: are activity and concentration more important than genotype?" Artherioscler Thromb Vasc Biol; 21:1451–1457.

Man et al. (1987) "D–aspartate in human brain." *J Neurochem* 48:510–515.

McLaughlin et al. (2000) "Apolipoprotein J/clusterin limits the severity of murine autoimmune myocarditis." J Clin Invest; 106:1105–1113.

Merrifield et al. (1995) "Retro and Retroenantio Analogs of Cecropin–Melittin Hybrids" *Proc Natl Acad Sci USA* 92: 3449–3453.

Mishra et al. (1994) "Interactions of Synthetic Peptide Analogs of the Class A" *J. Biol. Chem.* 269: 7185–7191.

Mishra et al. (1995) "Effect of the Arrangement of Tandem Repeating Units of Class A Amphipathic alpha–Helixes on Lipid Interaction." *J. Biol. Chem.* 270: 1602–1611.

Mishra et al. (1998) Studies of Synthetic Peptides of Human Apolipoprotein A–I Containing Tandem Amphipathic alpha–Helixes *Biochemistry 37*: 10313–10324.

Mitsuhashi et al. (1997) "Depletion of reactive advanced glycation endproducts from diabetic uremic sera using a lysozyme–linked matrix." J Clin Invest; 100: 847–854.

Mor et al. (1992) Enter a new post–translational modification: D–amino acids in gene–encoded peptides, *TIBS,* 17: 481–485.

Morrissey et al. (2001) "An antigen capture assay for the measurement of serum clusterin concentrations." J Biochem Biophys Methods;48: 13–21.

Nagata et al. (1994) "Distribution of free D–serine in vertebrate brains", *Brain Res.,* 634: 291–295.

Nagata et al. (1995) "Free D–serine concentration in normal and Alzheimer human brain", *Brain Res. Bull.,* 38(2): 181–183.

Navab et al. (1997) "Mildly oxidized LDL induces an increased apolipoprotein J/paraoxonase ratio." J Clin Invest; 99:2005–2019.

Navab et al. (2000) "Normal high–density lipoprotein inhibits three steps in the formation of midly oxidized low density lipoprotein: step 1." *J. Lipid Res.* 41: 1481–1494.

Navab et al. (2000) "Normal high–density lipoprotein inhibits three steps in the formation of mildly oxidized low density lipoprotein: steps 2 and 3." *J. Lipid Res.* 41: 1495–1508.

Navab et al. (2001) "HDL and the inflammatory response induced by LDL–derived oxidized phospholipids." Arterioscler Thromb Vasc Biol. 21:481–488.

Navab et al. (2002) "Oral Administration of an Apo A–I Mimetic Peptide Synthesized from D–Amino Acids Dramatically Reduces Atherosclerosis in Mice Independent of Plasma Cholesterol" *Circulation* 105: 290–292.

Newkirk et al. (1999) "Systemic lupus erythematosus, a disease associated with low levels of clusterin/apoJ, an anti–inflammatory protein." J Rheumatol; 26: 597–603.

Nishida et al. (1999) "Apolipoproteins J and E co–localise with amyloid in gelatinous drop–like and lattice type I corneal dystrophies." *Br J Ophthalmot;* 83: 1178–1182.

Nomoto et al. (1998) "Improved of intestinal absorbtion of peptide drugs by Gyycosylation: Transport of Tetrapeptide by the Sodium Ion–Dependent D–Glucose Transporter." *J. Pharmaceutics Science* 87(3):326–332.

Ohatani et al. (1995) Age–related changes in D–aspartic acid of rat teeth, *Growth Develop. & Aging,* 59: 55–61.

Oram and Yokoyama (1996) "Apolipoprotein–mediated removal of cellular cholesterol and phospholipids." *J. Lipid Res. 37:* 2473–2491.

Owens et al. (1990) "Apolipoprotein A–I and its Amphipathic Helix Peptide Analogues Inhibit Human Immunodeficiency Virus–Induced Syncytium Formation" *J Clin Invest* 86: 1142–1150.

Paigen et al. (1990) "Atherosclerosis Susceptibility Differences among Progenitors of Recombinant Inbred Strains of Mice." *Arteriosclerosis* 10: 316–323.

Palgunachari et al. (1996) "Only the Two End Xelises of Eight Tandem Amphipathic Helical Domaine of Human Apo A–I Have Significant Lipid Affinity." *Arteriosclerosis, Thrombosis, & Vascular Biology* 16: 328–338.

Panizzutti et al. (2001) "A New Strategy to Decrease N–methyl–D–aspartate (NMDA) Receptor Coactivation: Inhibition of D–serine Synthesis by Converting Serine Racemase into an Eliminase" *PNAS* 98:5294–5299.

Pappenheimer et al. (1994) "Intestinal Absorption and Excretion of Octapeptides Composed of D Amino Acids" *Proc Natl Acad Sci USA* 91: 1942–1945.

Pappenheimer et al. (1997) "Absorption and Excretion of Undegradable Peptides: Roles of Lipid Solubility and Net Charge." *J. Pharmacology & Experimental Therapeutics* 280(1):292–300.

Paszty et al. (1994) "Apolipoprotein AI Transgene Corrects Apolipoprotein E Deficiency–induced Atherosclerosis in Mice." *J. Clinical Investigation* 94:899–903.

Peng et al. (2001) "Effect of L–glutamate, D–aspartate, and Monensin on Glycolytic and Oxidative Glucose Metabolism in Mouse Astrocyte Cultures: Further Evidence that Glutamate Uptake is Metabolically Driven by Oxidative Metabolism" *Neurochem. Int'l* 38:437–443.

Pharmalicensing (Jan. 27, 2001) Esperion Builds a Novel Peptides Program (2 pages).

Pharmalicensing (Jan. 28, 2001) Multiple Peptide Systems Forms Joint Venture With Elan.

Pharmalicensing (Jan. 28, 2001) Unigene to Receive Patent for Delivery of Peptide Pharmaceuticals (2 pages).

Phillips et al. (1993) "Plasma Lipoproteins and Progression of Coronary Artery Disease Evaluated by Angiography and Clinical Events." *Circulation* 88: 2762–2770.

Pilone (2000) D–amino acid oxidase: a new findings. *CMSLS, Cell. Mol. Life Sci.,* 57: 1732–1747.

Plump et al. (1994) "Human apolipoprotein A–I gene expression increases high density lipoprotein and suppresses stherosclerosis in the apolipoprotein E–deficient mouse." *Proc. Natl. Acad. Sci.* USA 91:9607–9611.

Purdue News (Oct. 2000) 'Microspheres' Offer Promise for Oral Drug Delivery (3 pages).

Purdue News (Sep. 12, 1997) New Oral Insulin Delivery System Shows Promise (3 pages).

Redondo et al. (2000) "Overexpression of clusterin in human breast carcinoma." *Am J Pathol*; 157:393–399.

Reubsaet et al. (1999) "Qualitative and quantitative aspects of the degradation of several tripeptides derived from the antitumor peptide antagonist [$Arg^6$, $D-Trp^{7,9}$, $MePhe^8$] substance P{6–11}." *J. Pharmaceut. & Biomed Analysis* 19(3–4):277–284.

Rubin et al. (1991) "Inhibition of early atherogenesis in transgenic mice by human apolipoprotein AI." *Nature* 353:265–267.

Segrest et al. (1974) "A Molecular Theory of Lipid–Protein Interaction in the Plasma Lipoproteins." *FEBS Lett.* 38: 247–253.

Segrest et al. (1990) "Amphipathic Helix Motif: Classes and Properties." *Proteins: Structure, Function and Genetics* 8: 103–117.

Segrest et al. (1991) Erratum *Proteins: Structure, Function and Genetics* 9:79.

Segrest et al. (1992) "The Amphipathic Helix in the Exchangeable Apolipoproteins: A Review of Secondary Structure and Function" *J Lipid Research* 33:141–166.

Segrest et al. (1994) "The Amphipathic alpha Helix: A Multifunctional Structural Motif in Plasma Apolipoproteins." *Adv. Prot. Chem.* 45: 303–369.

Segrest et al. (2000) "Structure and function of apolipoprotein A–I and high–density lipoprotein." *Current Opin. Lipidol.* 11:105–115.

Senior (1999) "New options developed for needle–free drug delivery" *Lancet* Sep. 25, 1999.

Shah et al. (1998) "Effect of Recombinant Apolipoprotein A–I$_{Milano}$ on Aortic Atherosclerosis in Apolipoprptein E–Deficient Mice." *Circulation* 97:780–785.

Silkensen et al. (1999) "Identification of clusterin sequences mediating renal tubular cell interactions." *J. Pept Res*; 54: 449–457.

Singh et al. (2000) "Innate Defences Against Viraemia" *Rev Med Virol* 10:395–403.

Sprecher et al. (1993) "The Low HDL Cholesterol/High Triglyceride Trait." *Arterioscler. Thromb.* 13: 495–504.

Srinivas et al. (1990) "Antiviral Effects of Apolipoprotein A–I and Its Synthetic Amphipathic Peptide Analogs" *Virology* 176:48–57.

Starlix MC—Amino Acid Fact Sheet. http://www.starlix.com/media_center/content/pages/amino.htm (Dec. 10, 2002).

Steinberg et al. (1997) "Intracellular levels of SGP–2 (Clusterin) correlate with tumor grade in prostate cancer." *Clin Cancer Res*;3: 1707–1711.

Su and Amidon (1995) Investigation into the intestinal metabolism of [D–Ala] peptide T amide: implication for oral drug delivery, *Biochim et Biophys.*, 1245: 62–68.

The Wall Street Journal (Jan. 13, 2000) "Emisphere technologies develops oral Heparin".

Tsai et al. (1998) D–serine added to antipsychotics for the treatment of schizophrenia. *Biol. Psychiatry*, 44: 1081–1089.

Tsao et al. (2001) "Hibernation–induction Peptide and Cell Death: [$D-Ala^2$, $D-Leu^5$]enkephalin Blocks Bax–related Apoptotic Processes" *European Journal of Pharmacology* 428:149–151.

Tsimikas et al. (2001) "Measuring Circulating Oxidized Low–Density Lipoprotein to Evaluate Coronary Risk." *Circulation* 103:1930–1932.

Van Lenten et al. (2001) "High–density lipoprotein loses its anti–inflammatory properties during acute influenza a infection." *Circulation* 103:2283–2288.

Van Lenten et al. (2001) "Oxidized phospholipids induce changes in hepatic paraoxonase and ApoJ but not monocyte chemoattractant protein–1 via interleukin–6." *J Biol. Chem*;276: 1923–1929.

Venkatachalapathi et al. (1993) "Effect of End Group Blockage on the Properties of a Class A Amphipathic Helical Peptied." *Proteins:Structure, Function, and Genetics* 15:349–359.

Wehrli et al. (2001) "Inhibition of post–ischemic brain injury by clusterin overexpression." *Nature Medicine*; 7: 977–978.

\* cited by examiner

US 6,930,085 B2

G-TYPE PEPTIDES TO AMELIORATE ATHEROSCLEROSIS

STATEMENT AS TO RIGHTS TO INVENTIONS MADE UNDER FEDERALLY SPONSORED RESEARCH AND DEVELOPMENT

This work was supported, in part, by Grant No: HL30568 from the National Heart Blood Lung Institute of the National Institutes of Health. The Government of the United States of America may have certain rights in this invention.

CROSS-REFERENCE TO RELATED APPLICATIONS

[Not Applicable]

FIELD OF THE INVENTION

This invention relates to the field of atherosclerosis. In particular, this invention pertains to the identification of a class of peptides that are orally administrable and that ameliorate one or more symptoms of atherosclerosis or other pathologies characterized by an inflammatory response.

BACKGROUND OF THE INVENTION

The introduction of statins (e.g. Mevacor@, Lipitor@) has reduced mortality from heart attack and stroke by about one-third. However, heart attack and stroke remain the major cause of death and disability, particularly in the United States and in Western European countries. Heart attack and stroke are the result of a chronic inflammatory condition, which is called atherosclerosis.

Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Cholesterol is present in the blood as free and esterified cholesterol within lipoprotein particles, commonly known as chylomicrons, very low density lipoproteins (VLDLs), low density lipoproteins (LDLs), and high density lipoproteins (HDLs). Concentration of total cholesterol in the blood is influenced by (1) absorption of cholesterol from the digestive tract, (2) synthesis of cholesterol from dietary constituents such as carbohydrates, proteins, fats and ethanol, and (3) removal of cholesterol from blood by tissues, especially the liver, and subsequent conversion of the cholesterol to bile acids, steroid hormones, and biliary cholesterol.

Maintenance of blood cholesterol concentrations is influenced by both genetic and environmental factors. Genetic factors include concentration of rate-limiting enzymes in cholesterol biosynthesis, concentration of receptors for low density lipoproteins in the liver, concentration of rate-limiting enzymes for conversion of cholesterols bile acids, rates of synthesis and secretion of lipoproteins and gender of person. Environmental factors influencing the hemostasis of blood cholesterol concentration in humans include dietary composition, incidence of smoking, physical activity, and use of a variety of pharmaceutical agents. Dietary variables include amount and type of fat (saturated and polyunsaturated fatty acids), amount of cholesterol, amount and type of fiber, and perhaps amounts of vitamins such as vitamin C and D and minerals such as calcium.

Low density lipoprotein (LDL) oxidation has been strongly implicated in the pathogenesis of atherosclerosis. High density lipoprotein (HDL) has been found to be capable of protecting against LDL oxidation, but in some instances has been found to accelerate LDL oxidation. Important initiating factors in atherosclerosis include the production of LDL-derived oxidized phospholipids.

Normal HDL has the capacity to prevent the formation of these oxidized phospholipids and also to inactivate these oxidized phospholipids once they have formed. However, under some circumstances HDL can be converted from an anti-inflammatory molecule to a pro-inflammatory molecule that actually promotes the formation of these oxidized phospholipids.

HDL and LDL have been suggested to be part of the innate immune system (Navab et al. (2001) *Arterioscler Thromb Vasc Biol.* 21: 481–488). The generation of anti-inflammatory HDL has been achieved with class A amphipathic helical peptides that mimic the major protein of HDL, apolipoprotein A-I (apo A-I) (see, e.g., WO 02/15923).

SUMMARY OF THE INVENTION

This invention provides novel compositions and methods to ameliorate symptoms of atherosclerosis and other inflammatory conditions such as rheumatoid arthritis, lupus erythematous, polyarteritis nodosa, osteoporosis, Altzheimer's disease and viral illnesses such as influenza A.

In certain embodiments this invention provides "isolated" polypeptides that ameliorate a symptom of atherosclerosis or other pathologies associated with an inflammatory response and/or compositions comprising such polypeptides. The polypeptides typically comprise an amphipathic helical polypeptide having charged residues on the polar face of the polypeptide and possessing a wide non-polar face. The polypeptide is typically at least about 10 amino acids in length and/or about 40 or fewer polypeptides in length. Preferred polypeptides typically comprise a G* amphipathic helix. In certain embodiments, the polypeptides show greater than about 50%, preferably greater than about 75%, and more preferably greater than about 85% sequence identity with apo J (e.g. over a domain the same length as the polypeptide in question). Preferred polypeptides of this invention protect a phospholipid (e.g., 1-palmitoyl-2-arachidonoyl-sn-glycero-3-phosphorylcholine (PAPC), 1-stearoyl-2-arachidonoyl-sn-glycero-3-phosphorylcholine (SAPC)), 1-stearoyl-2-arachidonyl-sn-glycero-3-phosphorylethanolamine (SAPE)) against oxidation by an oxidizing agent (e.g., 13(S)-HPODE, 15(S)-HPETE, HPODE, HPETE, HODE, and HETE). Particularly preferred polypeptides comprise or consist of one or more of the following amino acid sequences: LLEQLNEQFNWVSRLANLTEGE, (SEQ ID NO:1), LLEQLNEQFNWVSRLANL, (SEQ ID NO:2), NELQEMSNQGSKYVNKEIQNAVNGV, (SEQ ID NO:3), IQNAVNG VKQIKTLIEKTNEE, (SEQ ID NO:4), RKTLLSNLEEAKKKKEDALNETRESETKLKEL, (SEQ ID NO:5), PGVCNETMMALWEECK, (SEQ ID NO:6), PCLKQTCMKFYARVCR, (SEQ ID NO:7), ECKPCLKQTCMKFYARVCR, (SEQ ID NO:8), LVGRQLEEFL, (SEQ ID NO:9), MNGDRIDSLLEN, (SEQ ID NO:10), QQTHMLDVMQD, (SEQ ID NO:11), FSRASSIIDELFQD, (SEQ ID NO:12), PFLEMIHEAQQAMDI, (SEQ ID NO:13), PTEFIREGDDD, (SEQ ID NO:14), RMKDQCDKCREILSV, (SEQ ID NO:15), PSQAKLRRELDESLQVAERLTRKYNELLKSYQ, (SEQ ID NO:16), LLEQLNEQFN WVSRLANLTQGE, (SEQ ID NO:17), DQYYLRVTTVA, (SEQ ID NO:18), PSGVTEVVVKLFDS, (SEQ ID NO:19), PKFMETVAEKALQEYRKKHRE, (SEQ ID NO:20), WDRVKDLATVYVDVLKDSGRDYVSQF (SEQ ID NO:21), VATVMWDYFSQ LSNNAKEAVEHLQK (SEQ ID NO:22), RWELALGRFWDYLRWVQTLSEQVQEEL (SEQ ID NO:23), LSSQVTQELRALMDET-MKELKELKAYKSELEEQLT (SEQ ID NO:24), ARL-SKELQAAQARLGADMEDVCGRLV (SEQ ID NO:25), VRLASHLRKLRKRLLRD ADDLQKRLA (SEQ ID NO:26), PLVEDMQRQWAGLVEKVQA (SEQ ID NO:27), MSTYTGIFTDQVLSVLK (SEQ ID NO:28), and LLSFM-QGYMKHATKTAKDALSS (SEQ ID NO:29). In certain embodiments, the polypeptide is a concatamer of two or more of these amino acid sequences and/or a concatamer of one or more of these amino acid sequences and an apo A-I sequence or a mimetic thereof (see, e.g., PCT publication WO 02/15923 for apo A-I related polypeptides/mimetics). The polypeptides of this invention can comprise a protecting group (e.g. a protecting group on the amino and/or carboxyl terminus). Preferred protecting groups include, but are not limited to acetyl, amide, 3 to 20 carbon alkyl groups, Fmoc, t-boc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2, 3,6-trimethyl-benzenesulphonyl (Mtr), Mesitylene-2-sulphonyl (Mts), 4,4=-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene) ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), a benzoyl group, a carbobenzoxy group, a propyl group, a butyl group, a pentyl group, a hexyl group, and Trifluoroacetyl (TFA). In certain embodiments, the polypeptide comprises a protecting group coupled to the amino terminal and the amino terminal protecting group is a protecting group such as a benzoyl group, an acetyl, a propeonyl, a carbobenzoxy, a propyl, a butyl, a pentyl, a hexyl, or a 3 to 20 carbon alkyl. In certain embodiments, the polypeptide comprises a protecting group coupled to the carboxyl terminal and the carboxyl terminal protecting group is an amide.

In particularly preferred embodiments, the polypeptide(s) of this invention comprise one or more dextro "D" amino acids. In certain embodiments, the polypeptide(s) of this invention comprise at least two, preferably at least 4, and most preferably all "D" amino acids.

In certain embodiments the polypeptide(s) described herein are covalently coupled to a phospholipid (e.g. lysophosphatidyl choline). In particularly preferred embodiments, the polypeptide(s) are coupled to the sn-1 or sn-2 position of a phospholipid (e.g. propionoyl, butanoyl, pentanoyl, caproyl, heptanoyl, capryloyl, nonanoyl, capryl, undcanoyl, lauroyl, tridecanoyl, myristoyl, pentadecanoyl, palmitoyl, heptadecanoyl, stearoyl, nonadecanoyl, arachidoyl, heniecosanoyl, behenoyl, trucisanoyl, lignoceroyl, myristoleoyl (9-cis), myristelaidoyl (9-trans), palmitoleoyl (9-cis), palmitelaidoyl (9-trans, and the like).

The polypeptide(s) of this invention can be formulated with a pharmacologically acceptable excipient (e.g. a unit dosage formulation for oral administration, rectal administration, nasal administration, injection, and the like).

In another embodiment, this invention provides a composition suitable for oral administration that ameliorates a symptom of atherosclerosis or other pathologies characterized by an inflammatory response. The composition comprises a polypeptide comprising an amphipathic helix (e.g. a G* helix) as described herein where the polypeptide comprises one or more "D" amino acids as described herein and the polypeptide is blocked at the amino terminus and the carboxyl terminus as described herein.

In certain embodiments, this invention provides pharmaceutical formulations (compositions). The pharmaceuticals comprise a polypeptide as described herein in a pharmaceutically acceptable excipient. The formulation is often a unit dosage formulation (e.g. for oral, rectal, nasal, or injectible administration to a mammal such as a human).

This invention also provides a method of method of ameliorating a symptom of atherosclerosis, or other pathology characterized by an inflammatory response in a mammal. The method involves administering to the mammal (e.g. a human) a polypeptide or a concatamer of a polypeptide comprising an amphipathic helical polypeptide having charged residues on the polar face of the polypeptide and possessing a wide non-polar face as described herein. In certain embodiments, the mammal is a human (e.g. a human diagnosed as having or as being at risk for atherosclerosis, stroke, or other pathology associated with an inflammatory response). In certain embodiments, the mammal is non-human mammal (e.g. canine, feline, bovine, equine, porcine, etc.).

In another embodiment, this invention provides a method of ameliorating a symptom of a pathology characterized by an inflammatory response (e.g. a symptom of rheumatoid arthritis, lupus erythematous, polyarteritis nodosa, osteoporosis, Altzheimer's disease and viral illnesses such as influenza A, etc). The method involves administering to the mammal (e.g. human) a polypeptide or a concatamer of a polypeptide comprising an amphipathic helical polypeptide having charged residues on the polar face of the polypeptide and possessing a wide non-polar face as described herein.

This invention also provides a kit for ameliorating a symptom of atherosclerosis or another pathology characterized by an inflammatory response. The kit typically includes a container containing one or more of the polypeptides described herein. The polypeptide(s) can be combined with a pharmaceutically acceptable excipient (e.g. in a unit dosage formulation for oral, nasal, rectal, injectible administration). The kit can additionally include instructional materials teaching the use of the polypeptide for ameliorating one or more symptoms of atherosclerosis or of a pathology characterized by an inflammatory response.

In still another embodiment, this invention provides a method of mitigating or preventing a coronary complication associated with an acute phase response to an inflammation in a mammal, wherein said coronary complication is a symptom of atherosclerosis. The method involves administering to a mammal having the acute phase response, or at risk for the acute phase response, one or more polypeptides described herein. The administration can be by a route such as oral administration, nasal administration, rectal administration, intraperitoneal injection, and intravascular injection, subcutaneous injection, transcutaneous administration, intramuscular injection, and the like. In certain embodiments, the polypeptide is administered in combination with an all L-form of the same polypeptide. In certain embodiments, the polypeptide(s) are provided as a unit formulation in a pharmaceutically acceptable excipient. The acute phase response can be an inflammatory response associated with a recurrent inflammatory disease. In certain embodiments, the acute phase response is associated with a disease including, but not limited to leprosy, tuberculosis, systemic lupus erythematosus, polymyalgia rheumatica, polyarteritis nodosa, scleroderma, idiopathic pulmonary fibrosis, chronic obstructive pulmonary disease, Alzheimers Disease and AIDS, polymyalgia rheumatica, polyarteritis nodosa, scleroderma, idiopathic pulmonary fibrosis, chronic obstructive pulmonary disease, Alzheimers Disease, AIDS, coronary calcification, calcific aortic stenosis, osteoporosis, and rheumatoid arthritis. In certain embodiments, the acute phase response is an inflammatory response associated with a condition such as a bacterial infection, a viral infection, a fungal infection, an organ transplant, a wound, an implanted prosthesis, parasitic infection, sepsis, endotoxic shock syndrome, and biofilm formation.

This invention also provides a method of mitigating or preventing a coronary complication associated with an acute phase response to an inflammation in a mammal where the coronary complication is a symptom of atherosclerosis. The method involves assaying the mammal (e.g. a human) for an acute phase protein (APP) level indicative of an acute phase response or a significant risk of an acute phase response; and administering to a mammal showing an acute phase protein (APP) level indicative of an acute phase response a polypeptide as described herein. The acute phase protein (APP) can be a positive APR such as serum amyloid A, c-reactive protein, serum amyloid P component, C2 complement protein, C3 complement protein, C4 complement protein, C5 complement protein, C9 complement protein, B complement protein, C1 inhibitor, C4 binding protein, fibrinogen, von Willebrand factor, $\alpha 1$-antitrypsin, $\alpha 1$-antichymotrypsin, $\alpha 2$ antiplasmin, heparin cofactor II, plasminogen activator inhibitor I, haptoglobin, haemopexin, ceruloplasmin, manganese superoxide dismutase, ($\alpha 1$-acid glycoprotein, haeme oxygenase, mannose binding protein, leukocyte protein I, lipoprotein (a), and lipopolysaccharide binding protein and/ or a negative APR such as consisting of albumin, prealbumin, transferin, apoAI, apoAII, $\alpha 2$-HS glycoprotein, inter-$\alpha$-trypsin inhibitor, histidine rich glycoprotein.

Definitions.

The terms "isolated", "purified", or "biologically pure" when referring to an isolated polypeptide refer to material that is substantially or essentially free from components that normally accompany it as found in its native state. With respect to nucleic acids and/or polypeptides the term can refer to nucleic acids or polypeptides that are no longer flanked by the sequences typically flanking them in nature. Chemically synthesized polypeptides are "isolated" because they are not found in a native state (e.g. in blood, serum, etc.). In certain embodiments, the term "isolated" indicates that the polypeptide is not found in nature.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "an amphipathic helical peptide" refers to a peptide comprising at least one amphipathic helix (amphipathic helical domain). Certain amphipathic helical peptides of this invention can comprise two or more (e.g. 3, 4, 5, etc.) amphipathic helices.

The term "class A amphipathic helix" refers to a protein structure that forms an $\alpha$-helix producing a segregation of a polar and nonpolar faces with the positively charged residues residing at the polar-nonpolar interface and the negatively charged residues residing at the center of the polar face (see, e.g., "Segrest et al. (1990) *Proteins: Structure, Function, and Genetics* 8: 103–117).

"Apolipoprotein J" (apo J) is known by a variety of names including clusterin, TRPM2, GP80, and SP 40,40 (Fritz (1995) Pp 112 In: *Clusterin: Role in Vertebrate Development, Function, and Adaptation* (Harmony JAK Ed.), R. G. Landes, Georgetown, Tex.,). It was first described as a heterodimeric glycoprotein and a component of the secreted proteins of cultured rat Sertoli cells (Kissinger et al. (1982) *Biol Reprod;* 27:233240). The translated product is a single-chain precursor protein that undergoes intracellular cleavage into a disulfide-linked 34 kDa $\alpha$subunit and a 47 kDa $\beta$subunit Collard and Griswold (187) *Biochem.,* 26: 3297–3303). It has been associated with cellular injury, lipid transport, apoptosis and it may be involved in clearance of cellular debris caused by cell injury or death. Clusterin has been shown to bind to a variety of molecules with high affinity including lipids, peptides, and proteins and the hydrophobic probe 1-anilino-8-naphthalenesulfonate (Bailey et al. (2001) *Biochem.,* 40: 11828–11840).

The class G amphipathic helix is found in globular proteins, and thus, the name class G. The feature of this class of amphipathic helix is that it possesses a random distribution of positively charged and negatively charged residues on the polar face with a narrow nonpolar face. Because of the narrow nonpolar face this class does not readily associate with phospholipid (see, Segrest et al. (1990) *Proteins: Structure, Function, and Genetics.* 8: 103–117; also see Erratum (1991) *Proteins: Structure, Function and Genetics,* 9: 79). Several exchangeable apolipoproteins possess similar but not identical characteristics to the G amphipathic helix. Similar to the class G amphipathic helix, this other class possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix (see Segrest et al. (1992) *J. Lipid Res.,* 33: 141–166; also see Anantharamaiah et al. (1993) Pp. 109–142 In: *The Amphipathic Helix,* Epand, R. M. Ed CRC Press, Boca Raton, Fla.). Computer programs to identify and classify amphipathic helical domains have been described by Jones et al.(1992) *J. Lipid Res.* 33: 287–296) and include, but are not limited to the helical wheel program (WHEEL or WHEEL/ SNORKEL), helical net program (HELNET, HELNET/ SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art.

The term "protecting group" refers to a chemical group that, when attached to a functional group in an amino acid (e.g. a side chain, an alpha amino group, an alpha carboxyl group, etc.) blocks or masks the properties of that functional group. Preferred amino-terminal protecting groups include, but are not limited to acetyl, or amino groups. Other amino-terminal protecting groups include, but are not limited to alkyl chains as in fatty acids, propeonyl, formyl and others. Preferred carboxyl terminal protecting groups include, but are not limited to groups that form amides or esters.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g. hydrogen peroxide, 13-(S)-HPODE, 15-(S)-HPETE, HPODE, HPETE, HODE, HETE, etc.).

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g. apo A-I, paraoxonase, platelet activating factor acetylhydrolase, etc.) that reduce oxidized lipids (e.g. in low density lipoproteins) or that protect oxidized lipids from oxidation by oxidizing agents.

The term "Group II HDL" refers to an HDL that offers reduced activity or no activity in protecting lipids from oxidation or in repairing (e.g. reducing) oxidized lipids.

The term "HDL component" refers to a component (e.g. molecules) that comprises a high density lipoprotein (HDL). Assays for HDL that protect lipids from oxidation or that repair (e.g. reduce oxidized lipids) also include assays for components of HDL (e.g. apo A-I, paraoxonase, platelet activating factor acetylhydrolase, etc.) that display such activity.

The term "human apo A-I peptide" refers to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g. cells of the vascular endothelium), and/or chemotaxis into the subendothelial space, and/or differentiation of monocytes into macrophages.

The term "absence of change" when referring to the amount of oxidized phospholipid refers to the lack of a detectable change, more preferably the lack of a statistically significant change (e.g. at least at the 85%, preferably at least at the 90%, more preferably at least at the 95%, and most preferably at least at the 98% or 99% confidence level). The absence of a detectable change can also refer to assays in which oxidized phospholipid level changes, but not as much as in the absence of the protein(s) described herein or with reference to other positive or negative controls.

The following abbreviations are used herein: PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phosphocholine; ChC18:2: cholesteryl linoleate; ChC18: 2-OOH: cholesteryl linoleate hydroperoxide; DMPC: 1,2-ditetradecanoyl-rac-glycerol-3-phosphocholine; PON: paraoxonase; HPF: Standardized high power field; PAPC: L-α-1-palmitoyl-2-arachidonoyl-sn-glycero-3-phosphocholine; BL/6: C57BL/6J; C3H: C3H/HeJ.

The term "conservative substitution" is used in reference to proteins or peptides to reflect amino acid substitutions that do not substantially alter the activity (specificity (e.g. for lipoproteins))or binding affinity (e.g. for lipids or lipoproteins)) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351–360. The method used is similar to the method described by Higgins & Sharp (1989) *CABIOS* 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA,* 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

DETAILED DESCRIPTION

Figure 1:
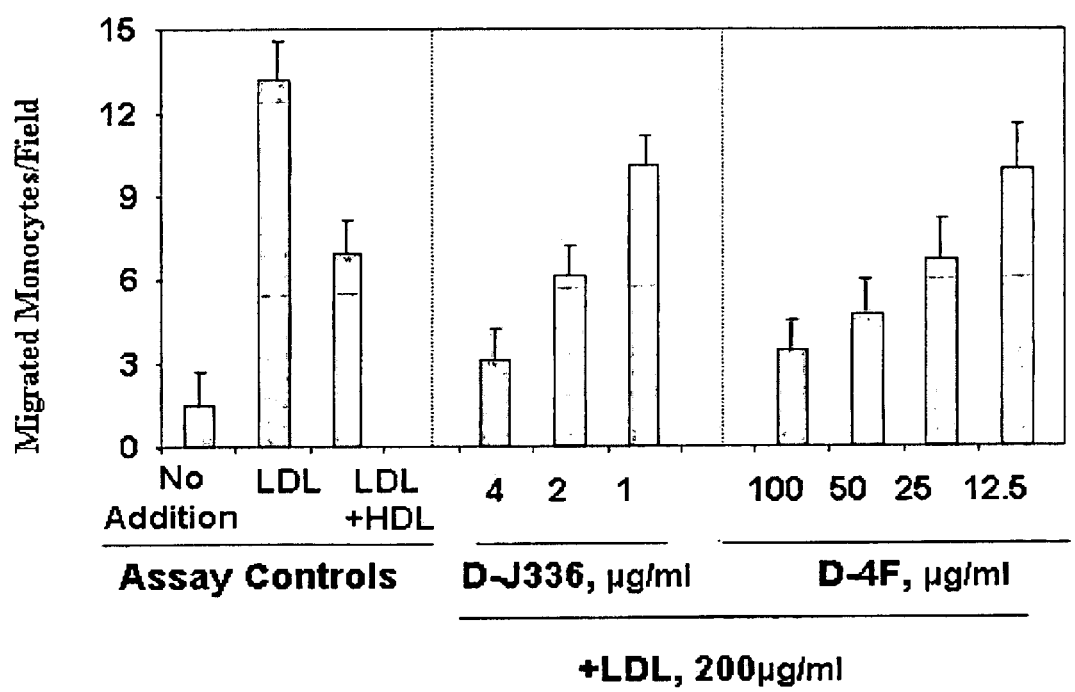
FIG. 1 shows a comparison of the effect of D4F (Navab, et al. (2002) *Circulation,* 105: 290–292) and apoJ peptide 336 made from D amino acids (D-J336*) on the prevention of LDL-induced monocyte chemotactic activity in vitro in a co-incubation experiment. The data are mean±SD of the number of migrated monocytes in nine high power fields in quadruple cultures. (D-J336=Ac-LLEQLNEQFNWVSRLANLTEGE-NH$_2$, SEQ ID NO:1).

I. Mitigation of a Symptom of Atherosclerosis.

This invention pertains to the surprising discovery that amphipathic helical peptide analogues possessing distributed (e.g. randomly distributed, haphazardly distributed, etc.) charged residues on the polar face of the peptide possess anti-inflammatory properties and are capable of mediating a symptom of atherosclerosis or other pathology characterized by an inflammatory response (e.g., rheumatoid arthritis, lupus erythematous, polyarteritis nodosa, and osteoporosis). Preferred peptides of this invention generally mimic the amphipathic helical domain(s) of apolipoprotein J (apo J).

In certain preferred embodiments, the peptides are amphipathic helical peptide analogues possessing distributed charged residues (positively and/or negatively charged residues) on the polar face of the peptide and possessing a wide nonpolar face (termed a globular protein like, G*)

amphipathic helical domain. Such amphipathic helical G* domains are characteristic of apo J and certain other apoproteins (e.g. apo AI, apo AIV, apo E, apo CII, apo CIII, and the like, but not apo A-II or apo C-I). The peptides of this invention preferably range from about 10 to about 100 amino acids in length, more preferably from about 10 to about 60 or 80 amino acids in length, and most preferably from about 10, 15, or 20 amino acids to about 40 or 50 amino acids in length. In certain embodiments, the peptides range from about 10 to about 40 amino acids in length. Certain particularly preferred peptides of this invention show greater than about 40%, preferably greater than about 50% or 60%, more preferably greater than about 70% or 80% and most preferably greater than about 90% or 95% sequence identity with apo J or fragments thereof (ranging in length from about 10 to about 40 amino acids, e.g. over the same length as the peptide in question).

It was a surprising discovery of this invention that such peptides, particularly when comprising one or more D-form amino acids retain the biological activity of the corresponding L-form peptide. Moreover, these peptides show in vivo activity, even when delivered orally. The peptides show elevated serum half-life, and the ability to mitigate or prevent/inhibit one or more symptoms of atherosclerosis.

We discovered that normal HDL inhibits three steps in the formation of mildly oxidized LDL. In those studies (see, e.g. WO 02/15923) we demonstrated that treating human LDL in vitro with apo A-I or an apo A-I mimetic peptide (37 pA) removed seeding molecules from the LDL that included HPODE and HPETE. These seeding molecules were required for cocultures of human artery wall cells to be able to oxidize LDL and for the LDL to induce the artery wall cells to produce monocyte chemotactic activity. We also demonstrated that after injection of apo A-I into mice or infusion into humans, the LDL isolated from the mice or human volunteers was resistant to oxidation by human artery wall cells and did not induce monocyte chemotactic activity in the artery wall cell cocultures.

Without being bound to a particular theory, we believe the peptides of this invention function in a manner similar to the activity of the apo A-I mimetics described in PCT publication WO 02/15923. In particular, we believe the present invention functions in part by increasing the antinflammatory properties of HDL. In particular, we believe the peptides of this invention bind seeding molecules in LDL that are necessary for LDL oxidation and then carry the seeding molecules away where there are ultimately excreted.

We have discovered that peptides that mimic the amphipathic helical domain(s) of apolipoprotein J are particularly effective in protecting LDL against oxidation by arterial wall cells and in reducing LDL-induced monocyte chemotactic activity that results from the oxidation of LDL by human artery wall cells. Apo J possesses a wide nonpolar face termed globular proteinlike, or G* amphipathic helical domains. The class G amphipathic helix is found in globular proteins, and thus, the name class G. The feature of this class of amphipathic helix is that it possesses a random/haphazard distribution of positively charged and negatively charged residues on the polar face with a narrow nonpolar face. Because of the narrow nonpolar face this class does not readily associate with phospholipid (see Segrest et al. (1990) *Proteins: Structure, Function, and Genetics.* 8: 103–117; also see Erratum (1991) *Proteins: Structure, Function and Genetics,* 9: 79). Several exchangeable apolipoproteins possess similar but not identical characteristics to the G amphipathic helix. Similar to the class G amphipathic helix, this other class possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix (see Segrest et al. (1992) *J. Lipid Res.,* 33: 141–166; also see Anantharamaiah et al. (1993) Pp. 109–142 *In The Amphipathic Helix,* Epand, R. M. Ed., CRC Press, Boca Raton, Fla.).

It was a surprising discovery of this invention that the amphipathic helical peptides of this invention required to render human artery wall cells incapable of oxidizing LDL was substantially less than that required for apo AI mimetic peptides such as D4F in a preincubation with artery wall cells.

We have demonstrated that oral administration of an apo AI mimetic peptide synthesized from D amino acids dramatically reduces atherosclerosis in mice independent of changes in plasma or HDL cholesterol concentrations. Similar to the action of the apo A-I mimetics, we believe that synthetic peptides mimicking the amphipathic helical domains of apo J that are synthesized from D amino acids can be given orally or by other routes including injection and will ameliorate atherosclerosis and other chronic inflammatory conditions.

The peptides of this invention can comprise all L-form amino acids. However, the inventors believe peptides comprising one or more D-form amino acids and preferably all D-form amino acids (all enantiomeric amino acids are D form) provide for more effective delivery via oral administration and will be more stable in the circulation. Particularly preferred peptides are blocked at one or both termini (e.g. with the N-terminus acetylated and the C-terminus amidated).

The protective function of the peptides of this invention is illustrated in Example 1. The in vitro concentration of the new class of peptides necessary to prevent LDL-induced monocyte chemotactic activity by human artery wall cells is 10 to 25 times less than the concentration required for an apoA-I mimetic (D4F) (compare DJ336 to D4F in FIG. 1). Similarly, in a preincubation the peptides of this invention were 1025 times more potent in preventing LDL oxidation by artery wall cells (compare DJ336 to D4F in FIG. 2). As shown in FIG. 3, when DJ335 was given orally to LDL receptor null mice it was essentially as effective as D4F in rendering HDL more protective in preventing LDL-induced monocyte chemotactic activity.

Figure 4:
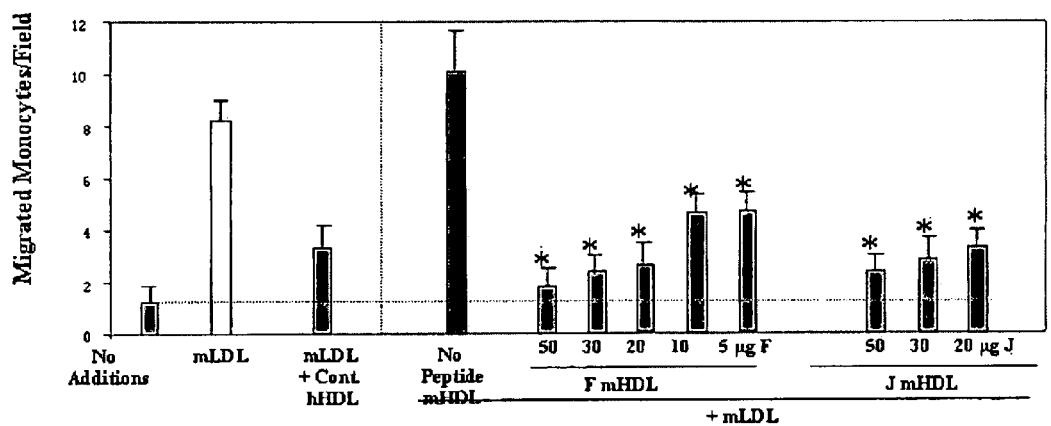
FIG. 4 illustrates protection against LDL-induced monocyte chemotactic activity by HDL from apo E null mice given oral peptides. The values are the mean±SD of the number of migrated monocytes in 9 high power fields from each of quadruple assay wells. Asterisks indicate significant difference (p<0.05) as compared to No Peptide mHDL.
Figure 5:
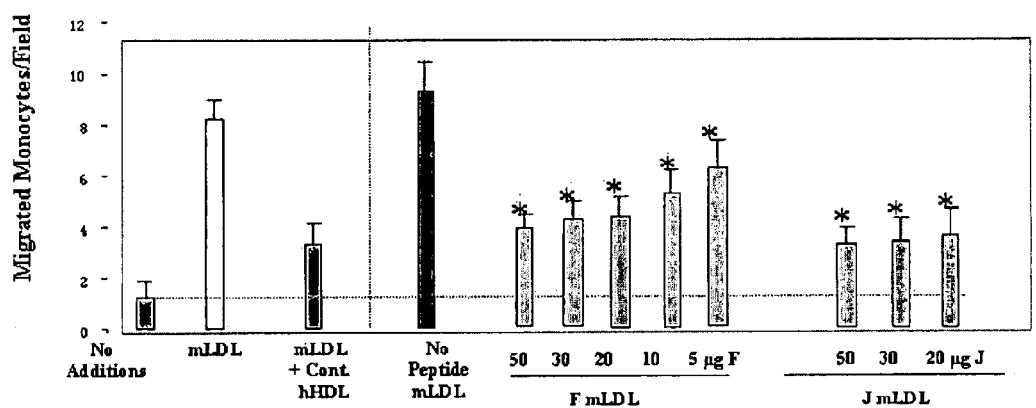
FIG. 5 illustrates the effect of oral apo A-I peptide mimetic and apoj peptide on LDL susceptibility to oxidation. The values are the mean±SD of the number of migrated monocytes in 9 high power fields from each of quadruple assay wells. Asterisks indicate significant difference (p<0.05) as compared to No Peptide LDL.
Figure 6:
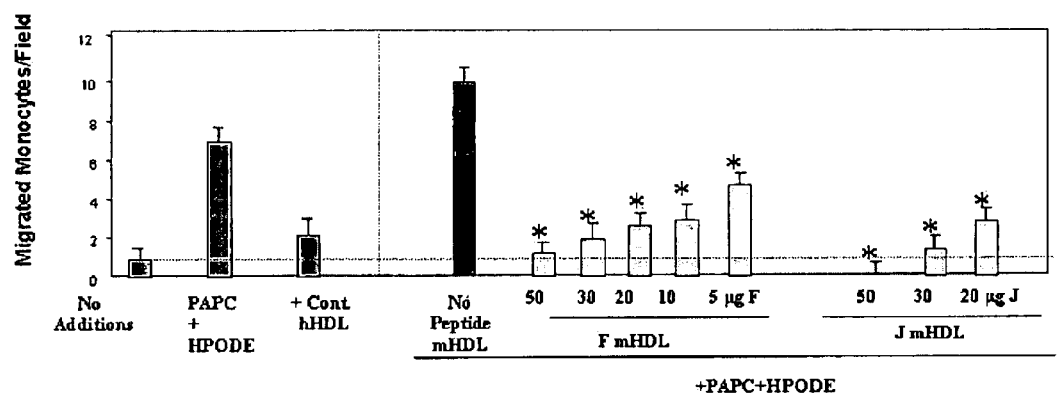
FIG. 6 illustrates the effect of oral apoA-1 peptide mimetic and apoJ peptide on HDL protective capacity. The values are the mean±SD of the number of migrated monocytes in 9 high power fields from each of quadruple assay wells. Asterisks indicate significant difference (p<0.05) as compared to No Peptide mHDL.
Figure 7:
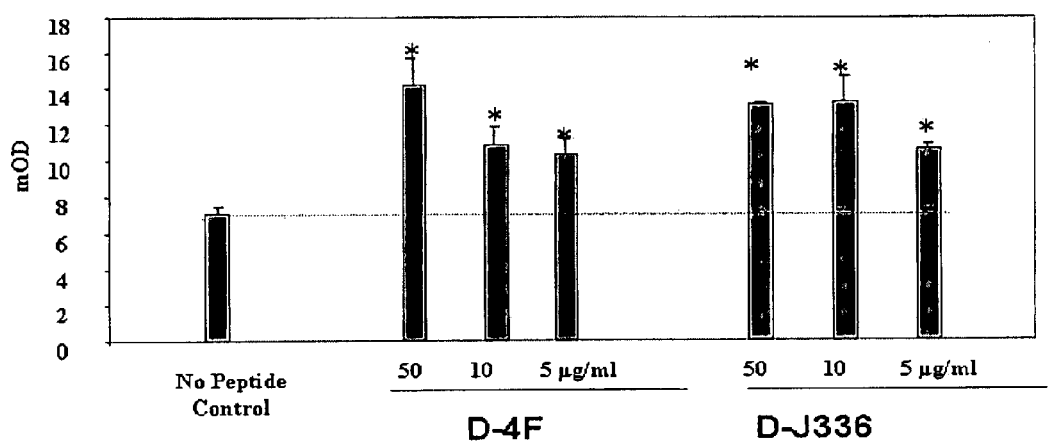
FIG. 7 illustrates the Effect of oral apoA-1 peptide mimetic and apoj peptide on plasma paraoxonase activity. The values are the mean±SD of readings from quadruple plasma aliquots. Asterisks indicate significant differences (p<0.05) as compared to No Peptide control plasma.

FIG. 4 demonstrates that when added to the drinking water a peptide of this invention (DJ336) was as potent as D4F in enhancing HDL protective capacity in apo E null mice. FIG. 5 demonstrates that, when added to the drinking water, a peptide of this invention DJ336 was slightly more potent than D4F in rendering the LDL from apo E null mice resistant to oxidation by human artery wall cells as determined by the induction of monocyte chemotactic activity. FIG. 6 demonstrates that when added to the drinking water DJ336 was as potent as D4F in causing HDL to inhibit the oxidation of a phospholipid PAPC by the oxidant HPODE in a human artery wall coculture as measured by the generation of monocyte chemotactic activity (see Navab et al. (2001) *J. Lipid Res.* 42: 1308–1317 for an explanation of the test system). FIG. 7 demonstrates that, when added to the drinking water, DJ336 was at least as potent as D4F in increasing the paraoxonase activity of apo E null mice.

Since many inflammatory conditions have been suspected to be mediated at least in part by oxidized lipids, we believe that this invention is also effective in ameliorating conditions that are known or suspected to be due to the formation of oxidized lipids. These include, but are not limited to, rheumatoid arthritis, lupus erythematous, polyarteritis nodosa, and osteoporosis.

Without being bound to a particular theory, we believe administration (e.g. injection) of one or more of the peptides of this invention will ameliorate the signs and symptoms of influenza A. In addition, the peptide will dramatically reduced the influx of macrophages into the artery wall. This will have great utility in reducing the high rate of heart attack and stroke after influenza and other viral infections. Thus, the peptides of this invention can be used to ameliorate the signs and symptoms of influenza and various other viral illnesses and reduce the incidence of heart attack and stroke that often follows these viral illnesses.

In view of the foregoing, in one embodiment, this invention provides methods for ameliorating and/or preventing one or more symptoms of atherosclerosis and/or a pathology associated with (characterized by) an inflammatory response. The methods typically involve administering to an organism, preferably a mammal, more preferably a human one or more of the peptides of this invention (or mimetics of such peptides). The peptide(s) can be administered, as described herein, according to any of a number of standard methods including, but not limited to injection, suppository, nasal spray, time-release implant, transdermal patch, and the like. In one particularly preferred embodiment, the peptide (s) are administered orally (e.g. as a syrup, capsule, or tablet).

The methods involve the administration of a single polypeptide of this invention or the administration of two or more different polypeptides. The polypeptides can be provided as monomers or in dimeric, oligomeric or polymeric forms. In certain embodiments, the multimeric forms may comprise associated monomers (e.g. ionically or hydrophobically linked) while certain other multimeric forms comprise covalently linked monomers (directly linked or through a linker).

While the invention is described with respect to use in humans, it is also suitable for animal, e.g. veterinary use. Thus preferred organisms include, but are not limited to humans, non-human primates, canines, equines, felines, porcines, ungulates, largomorphs, and the like.

The methods of this invention are not limited to humans or non-human animals showing one or more symptom(s) of atherosclerosis (e.g. hypertension, plaque formation and rupture, reduction in clinical events such as heart attack, angina, or stroke, high levels of plasma cholesterol, high levels of low density lipoprotein, high levels of very low density lipoprotein, or inflammatory proteins, etc.), but are useful in a prophylactic context. Thus, the peptides of this invention (or mimetics thereof) may be administered to organisms to prevent the onset/development of one or more symptoms of atherosclerosis. Particularly preferred subjects in this context are subjects showing one or more risk factors for atherosclerosis (e.g. family history, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

In addition to methods of use of the atherosclerosis-inhibiting peptides of this invention, this invention also provides the peptides themselves, the peptides formulated as pharmaceuticals, particularly for oral delivery, and kits for the treatment and/or prevention of one or more symptoms of atherosclerosis.

II. Mitigation of a Symptom of Atherosclerosis Associated with an Acute Inflammatory Response.

The atherosclerosis-inhibiting peptides of this invention are also useful in a number of other contexts. In particular, we have observed that cardiovascular complications (e.g. atherosclerosis, stroke, etc.) frequently accompany or follow the onset of an acute phase inflammatory response. Such an acute state inflammatory response is often associated with a recurrent inflammatory disease (e.g., leprosy, tuberculosis, systemic lupus erythematosus, and rheumatoid arthritis), a viral infection (e.g. influenza), a bacterial infection, a fungal infection, an organ transplant, a wound or other trauma, an implanted prosthesis, a biofilm, and the like.

It was a surprising discovery of this invention that administration of one or more of the peptides described herein, can reduce or prevent the formation of oxidized phospholipids during or following an acute phase response and thereby mitigate or eliminate cardiovascular complications associated with such a condition.

Thus, for example, we have demonstrated that a consequence of influenza infection is the diminution in paraoxonase and platelet activating acetylhydrolase activity in the HDL. Without being bound by a particular theory, we believe that, as a result of the loss of these HDL enzymatic activities and also as a result of the association of pro-oxidant proteins with HDL during the acute phase response, HDL is no longer able to prevent LDL oxidation and was no longer able to prevent the LDL-induced production of monocyte chemotactic activity by endothelial cells.

We observed that in a subject injected with very low dosages of apo-AI mimetics (e.g. 20 micrograms for mice) daily after infection with the influenza A virus paraoxonase levels did not fall and the biologically active oxidized phospholipids were not generated beyond background (see, e.g., WO 02/15923, PCT/US01/26497).

It was surprising discovery that the class of peptides described herein can act in manner similar to the apo-I mimetics described in WO 02/15923. In view of this discovery, it is believed that the peptides of this invention can be administered (e.g. orally or by injection) to patients with known coronary artery disease during influenza infection or other events that can generate an acute phase inflammatory response (e.g. due to viral infection, bacterial infection, trauma, transplant, various autoimmune conditions, etc.) and thus we can prevent by this short term treatment the increased incidence of heart attack and stroke associated with pathologies that generate such inflammatory states.

Thus, in certain embodiments, this invention contemplates administering one or more of the peptides of this invention to a subject at risk for, or incurring, an acute inflammatory response and/or at risk for or incurring a symptom of atherosclerosis.

For example, a person having or at risk for coronary disease may prophylactically be administered a polypeptide of this invention during flu season. A person (or animal) subject to a recurrent inflammatory condition, e.g. rheumatoid arthritis, various autoimmune diseases, etc., can be treated with a polypeptide of this invention to mitigate or prevent the development of atherosclerosis or stroke. A person (or animal) subject to trauma, e.g. acute injury, tissue transplant, etc. can be treated with a polypeptide of this invention to mitigate the development of atherosclerosis or stroke.

In certain instances such methods will entail a diagnosis of the occurrence or risk of an acute inflammatory response. The acute inflammatory response typically involves alterations in metabolism and gene regulation in the liver. It is a dynamic homeostatic process that involves all of the major systems of the body, in addition to the immune, cardiovascular and central nervous system. Normally, the acute phase response lasts only a few days; however, in cases of chronic or recurring inflammation, an aberrant continuation of some aspects of the acute phase response may contribute to the underlying tissue damage that accompanies the disease, and may also lead to further complications, for example cardiovascular diseases or protein deposition diseases such as amyloidosis.

An important aspect of the acute phase response is the radically altered biosynthetic profile of the liver. Under normal circumstances, the liver synthesizes a characteristic range of plasma proteins at steady state concentrations. Many of these proteins have important functions and higher plasma levels of these acute phase reactants (APRs) or acute phase proteins (APPs) are required during the acute phase response following an inflammatory stimulus. Although most APRs are synthesized by hepatocytes, some are produced by other cell types, including monocytes, endothelial cells, fibroblasts and adipocytes. Most APRs are induced between 50% and several-fold over normal levels. In contrast, the major APRs can increase to 1000-fold over normal levels. This group includes serum amyloid A (SAA) and either C-reactive protein (CRP) in humans or its homologue in mice, serum amyloid P component (SAP). So-called negative APRs are decreased in plasma concentration during the acute phase response to allow an increase in the capacity of the liver to synthesize the induced APRs.

In certain embodiments, the acute phase response, or risk therefore is evaluated by measuring one or more APPs. Measuring such markers is well known to those of skill in the art, and commercial companies exist that provide such measurement (e.g. AGP measured by Cardiotech Services, Louisville, Ky.).

III. Mitigation of a Symptom or Condition Associated with Coronary Calcification and Osteoporosis.

We have also identified oxidized lipids as a cause of coronary calcification and osteoporosis. Moreover, without being bound to a particularly theory, we believe the same mechanisms are involved in the pathogenesis of calcific aortic stenosis.

Thus, in certain embodiments, this invention contemplates the use of the peptides described herein to inhibit or prevent a symptom of a disease such as polymyalgia rheumatica, polyarteritis nodosa, scleroderma, idiopathic pulmonary fibrosis, chronic obstructive pulmonary disease, Alzheimers Disease, AIDS, coronary calcification, calcific aortic stenosis, osteoporosis, and the like.

IV. Preferred Peptides and their Preparation.

Preferred Peptides.

It was a discovery of this invention that peptides that mimicking the amphipathic helical domains of apo J are capable of mitigating one or more symptoms of atherosclerosis and/or other pathologies characterized by an inflammatory response. Apolipoprotein J possesses a wide nonpolar face termed globular protein-like, or G* amphipathic helical domains. The class G amphipathic helix is found in globular proteins, and thus, the name class G. This class of amphipathic helix is characterized by a random distribution of positively charged and negatively charged residues on the polar face with a narrow nonpolar face. Because of the narrow nonpolar face this class does not readily associate with phospholipids. The G* of amphipathic helix possesses similar, but not identical, characteristics to the G amphipathic helix. Similar to the class G amphipathic helix, the G* class peptides possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix.

A variety of suitable peptides of this invention that are related to G* amphipathic helical domains of apo J are illustrated in Table 1.

TABLE 1

Preferred peptides for use in this invention related to g* amphipathic helical domains of apo J.

| Amino Acid Sequence | SEQ ID NO |
|---|---|
| LLEQLNEQFNWVSRLANLTEGE | 1 |
| LLEQLNEQFNWVSRLANL | 2 |
| NELQEMSNQGSKYVNKEIQNAVNGV | 3 |
| IQNAVNGVKQIKTLIEKTNEE | 4 |
| RKTLLSNLEEAKKKKEDALNETRESETKLKEL | 5 |
| PGVCNETMMALWEECK | 6 |
| PCLKQTCMKFYARVCR | 7 |
| ECKPCLKQTCMKFYARVCR | 8 |
| LVGRQLEEFL | 9 |
| MNGDRIDSLLEN | 10 |
| QQTHMLDVMQD | 11 |
| FSRASSIIDELFQD | 12 |
| PFLEMTHEAQQAMDI | 13 |
| PTEFTREGDDD | 14 |
| RMKDQCDKCREILSV | 15 |
| PSQAKLRRELDESLQVAERLTRKYNELLKSYQ | 16 |
| LLEQLNEQFNWVSRLANLTQGE | 17 |
| DQYYLRVTTVA | 18 |
| PSGVTEVVVKLFDS | 19 |
| PKFMETVAEKALQEYRKKHRE | 20 |

The peptides of this invention, however, are not limited to G* variants of apo J. Generally speaking G* domains from essentially any other protein preferably apo proteins are also suitable. The particular suitability of such proteins can readily be determined using assays for protective activity (e.g. protecting LDL from oxidation, and the like), e.g. as illustrated herein in the Examples. Some particularly preferred proteins include G* amphipathic helical domains or variants thereof (e.g. conservative substitutions, and the like) of proteins including, but not limited to apo AI, apo AIV, apo E, apo CII, apo CIII, and the like.

Certain preferred peptides for related to G* amphipathic helical domains related to apoproteins other than apo J are illustrated in Table 2.

TABLE 2

Peptides for use in this invention related to G* amphipathic helical domains related to apoproteins other than apo J.

| Amino Acid Sequence | SEQ ID NO |
|---|---|
| WDRVKDLATVYVDVLKDSGRDYVSQF (Related to the 8 to 33 region of apo AI) | 21 |
| VATVMWDYFSQLSNNAKEAVEHLQK (Related to the 7 to 31 region of apo AIV) | 22 |
| RWELALGRFWDYLRWVQTLSEQVQEEL (Related to the 25 to 51 region of apo E) | 23 |
| LSSQVTQELRALMDETMKELKELKAYKSELEEQLT (Related to the 52 to 83 region of apo E) | 24 |
| ARLSKELQAAQARLGADMEDVCGRLV (Related to the 91 to 116 region of apo E) | 25 |
| VRLASHLRKLRKRLLRDADDLQKRLA (Related to the 135 to 160 region of apo E) | 26 |
| PLVEDMQRQWAGLVEKVQA (267 to 285 of apo E.27) | 27 |
| MSTYTGIFTDQVLSVLK (Related to the 60 to 76 region of apo CII) | 28 |
| LLSFMQGYMKHATKTAKDALSS (Related to the 8 to 29 region of apo CIII) | 29 |

While the various peptides listed in Table 1 and Table 2 are shown with no protecting groups, in certain embodiments (e.g. particularly for oral administration), they bear one or two protecting groups, more preferably terminal protecting groups. Thus, for example, in certain embodiments, any of the peptides descry bed herein can bear, e.g. an acetyl group protecting the amino terminus and/or an amide group protecting the carboxyl terminus. One example of such a "dual protected peptide is Ac-L-L-E-Q-L-N-E-Q-F-N-W-V-S-R-L-A-N-L-T-E-G-E-NH$_2$ (SEQ ID NO:1 with blocking groups), either or both of these protecting groups can be eliminated and/or substituted with another protecting group as described herein. In particularly preferred embodiments, the peptides comprise one or more D-form (dextro rather than levo) amino acids as described herein. In certain embodiments at least two enantiomeric amino acids, more preferably at least 4 enantiomeric amino acids and most preferably at least 8 or 10 enantiomeric amino acids are "D" form amino acids. In certain embodiments every amino acid (e.g. every enantiomeric amino acid) of the peptides described herein is a D-form amino acid.

It is also noted that the peptides listed in Tables 1 and 2 are not fully inclusive. Using the teaching provided herein, other suitable peptides can routinely be produced (e.g. by conservative or semi-conservative substitutions (e.g. D replaced by E), extensions, deletions, and the like). Thus, for example, one embodiment utilizes truncations of any one or more of peptides identified by SEQ ID Nos: 1–29.

Longer peptides are also suitable. Such longer peptides may entirely form a class G or G* amphipathic helix, or the G amphipathic helix (helices) can form one or more domains of the peptide. In addition, this invention contemplates multimeric versions of the peptides. Thus, for example, the peptides illustrated in Tables 1 or 2 can be coupled together (directly or through a linker (e.g. a carbon linker, or one or more amino acids) with one or more intervening amino acids). Suitable linkers include, but are not limited to Proline (-Pro-), Gly$_4$Ser$_3$ (SEQ ID NO:30), and the like. Thus, one illustrative multimeric peptide according to this invention is (D-J336)-P-(D-J336) (i.e. Ac-L-L-E-Q-L-N-E-Q-F-N-W-V-S-R-L-A-N-L-T-E-G-E-P-L-L-E-Q-L-N-E-Q-F-N-W-V-S-R-L-A-N-L-T-E-G-E-NH$_2$, SEQ ID NO:31).

This invention also contemplates the use of "hybrid" peptides comprising a one or more G or G* amphipathic helical domains and one or more class A amphipathic helices. Suitable class A amphipathic helical peptides are described in PCT publication WO 02/15923. Thus, by way of illustration, one such "hybrid" peptide is (D-J336)-Pro-(4F) (i.e. Ac-L-L-E-Q-L-N-E-Q-F-N-W-V-S-R-L-A-N-L-T-E-G-E-P-D-W-F-K-A-F-Y-D-K-V-A-E-K-F-K-E-A-F-NH$_2$, SEQ ID NO:32), and the like. As indicated above, the peptides of this invention preferably comprise one or more D amino acids, more preferably with every amino acid a D amino acid as described herein and/or having one or both termini protected. Preferably at least 50% of the enantiomeric amino acids are "D" form, more preferably at least 80% of the enantiomeric amino acids are "D" form, and most preferably at least 90% or even all of the enantiomeric amino acids are "D" form amino acids.

It was a surprising discovery of this invention that, when the amphipathic helical peptides of this invention (e.g. as illustrated in FIGS. 3, 4, 5, 6, and 7) incorporated D amino acids they retained their activity even when administered orally. Moreover this oral administration resulted in relatively efficient uptake and significant serum half-life thereby providing an efficacious method of mitigating one or more symptoms of atherosclerosis and/or other conditions characterized by an inflammatory response.

Using the teaching provided herein, one of skill can routinely modify the illustrated amphipathic helical peptides to produce other suitable apo J variants and/or amphipathic G helical peptides of this invention. For example, routine conservative or semi-conservative substitutions (e.g. E for D) can be made of the existing amino acids. The effect of various substitutions on lipid affinity of the resulting peptide can be predicted using the computational method described by Palgunachari et al. (1996) *Arteriosclerosis, Thrombosis, & Vascular Biology* 16: 328–338. The peptides can be lengthened or shortened as long as the class helix structure (s) are preserved. In addition, substitutions can be made to render the resulting peptide more similar to peptide(s) endogenously produced by the subject species.

New peptides can be designed and/or evaluated using computational methods. Computer programs to identify and classify amphipathic helical domains are well known to those of skill in the art and many have been described by Jones et al.(1992) *J. Lipid Res.* 33: 287–296). Such programs include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

While, in preferred embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

In addition to the G* amphipathic helical peptides described herein, peptidomimetics are also contemplated herein. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) *Adv. Drug Res.* 15: 29; Veber and Freidinger (1985) *TINS* p. 392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (e.g. SEQ ID NO:1 shown in Table 1), but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, —CH$_2$SO—, etc by methods known in the art and further described in the following references: Spatola (1983) p. 267 in *Chemistry and Biochemistry of Amino Acids, Peptides, and Proteins*, B. Weinstein, eds., Marcel Dekker, New York,; Spatola (1983) *Vega Data* 1(3) *Peptide Backbone Modifications*. (general review); Morley (1980) *Trends Pharm Sci* pp. 463–468 (general review); Hudson et al. (1979) *Int J Pept Prot Res* 14:177–185 (—CH$_2$NH—, CH$_2$CH$_2$—); Spatola et al. (1986) *Life Sci* 38: 1243–1249 (—CH$_2$—S); Hann, (1982) *J Chem Soc Perkin Trans* I 1307–314 (—CH=CH—, cis and trans); Almquist et al. (1980) *J Med Chem.* 23:1392–1398 (—COCH$_2$—); Jennings-White et al.(1982) *Tetrahedron Lett.* 23:2533 (—COCH$_2$—); Szelke et al., European Appln. EP 45665 (1982) CA: 97:39405 (1982) (—CH(OH)CH2-); Holladay et al. (1983) *Tetrahedron Lett* 24:4401–4404 (—C(OH)CH$_2$—); and Hruby (1982) *Life Sci.*, 31:189–199 (—CH$_2$—S—)).

A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circularly permutations of the peptides described herein or constrained peptides (including cyclized peptides) comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide.

Peptide Preparation.

The peptides used in this invention can be chemically synthesized using standard chemical peptide synthesis techniques or, particularly where the peptide does not comprise "D" amino acid residues, can be recombinantly expressed. In certain embodiments, even peptides comprising "D" amino acid residues are recombinantly expressed. Where the polypeptides are recombinantly expressed, a host organism (e.g. bacteria, plant, fungal cells, etc.) in cultured in an environment where one or more of the amino acids is provided to the organism exclusively in a D form. Recombinantly expressed peptides in such a system then incorporate those D amino acids.

In preferred embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis;* pp. 3–284 in *The Peptides: Analysis, Synthesis, Biology. Vol.* 2: *Special Methods in Peptide Synthesis, Part A.;* Merrifield et al. (1963) *J. Am. Chem. Soc.,* 85: 2149–2156, and Stewart et al. (1984) *Solid Phase Peptide Synthesis,* 2nd ed. Pierce Chem. Co., Rockford, Ill.

In a most preferred embodiment, the peptides are synthesized by the solid phase peptide synthesis procedure using a benzhyderylamine resin (Beckman Bioproducts, 0.59 mmol of NH$_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are described in a miniprint supplement accompanying Anantharamaiah et al. (1985) *J. Biol. Chem.,* 260(16): 10248–10255.

It is noted that in the chemical synthesis of peptides, particularly peptides comprising D amino acids, the synthesis usually produces a number of truncated peptides in addition to the desired full-length product. The purification process (e.g. HPLC) typically results in the loss of a significant amount of the full-length product.

It was a discovery of this invention that, in the synthesis of a D peptide (e.g. D-4), in order to prevent loss in purifying the longest form one can dialyze and use the mixture and thereby eliminate the last HPLC purification. Such a mixture loses about 50% of the potency of the highly purified product (e.g. per wt of protein product), but the mixture contains about 6 times more peptide and thus greater total activity.

D-form Amino Acids.

D-amino acids are incorporated at one or more positions in the peptide simply by using a D-form derivatized amino acid residue in the chemical synthesis. D-form residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form amino acids can be incorporated at any position in the peptide as desired. Thus, for example, in one embodiment, the peptide can comprise a single D-amino acid, while in other embodiments, the peptide comprises at least two, generally at least three, more generally at least four, most generally at least five, preferably at least six, more preferably at least seven and most preferably at least eight D amino acids. In particularly preferred embodiments, essentially every other (enantiomeric) amino acid is a D-form amino acid. In certain embodiments at least 90%, preferably at least 90%, more preferably at least 95% of the enantiomeric amino acids are D-form amino acids. In one particularly preferred embodiment, essentially every enantiomeric amino acid is a D-form amino acid.

Protecting Groups.

In certain embodiments, the one or more R-groups on the constituent amino acids and/or the terminal amino acids are blocked with a protecting group. Without being bound by a particular theory, it was a discovery of this invention that blockage, particularly of the amino and/or carboxyl termini of the subject peptides of this invention greatly improves oral delivery and significantly increases serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3$—$(CH_2)_n$—$CO$— where n ranges from about 1 to about 20, preferably from about 1 to about 16 or 18, more preferably from about 3 to about 13, and most preferably from about 3 to about 10.

In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g. groups having the formula: $CH_3$—$(CH_2)_n$—$CO$— where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO),t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis,* 2nd ed., John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semi-permanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

V. Enhancing Peptide Uptake.

It was also a surprising discovery of this invention that when an all L amino acid peptide (e.g. otherwise having the sequence of the peptides of this invention) is administered in conjunction with the D-form (i.e. a peptide of this invention) the uptake of the D-form peptide is increased. Thus, in certain embodiments, this invention contemplates the use of combinations of D-form and L-form peptides in the methods of this invention. The D-form peptide and the L-form peptide can have different amino acid sequences, however, in preferred embodiments, they both have amino acid sequences of peptides described herein, and in still more preferred embodiments, they have the same amino acid sequence.

It was also a discovery of this invention that concatamers of the amphipathic helix peptides of this invention are also effective in mitigating one or more symptoms of atherosclerosis. The monomers comprising the concatamers can be coupled directly together or joined by a linker. In certain embodiments, the linker is an amino acid linker (e.g. a proline), or a peptide linker (e.g. $Gly_4Ser_3$, SEQ ID NO:30). In certain embodiments, the concatamer is a 2 mer, more preferably a 3 mer, still more preferably a 4 mer, and most preferably 5 mer, 8 mer or 10 mer. As indicated above, the concatamer can comprise a G* related amphipathic helix as described herein combined with an apo A-I variant as described in PCT publication WO 02/15923.

VI. Pharmaceutical Formulations.

In order to carry out the methods of the invention, one or more peptides or peptide mimetics of this invention are administered, e.g. to an individual diagnosed as having one or more symptoms of atherosclerosis, or as being at risk for atherosclerosis. The peptides or peptide mimetics can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology, that typically involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the peptides or mimetics are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The peptides or mimetics identified herein are useful for parenteral, topical, oral, nasal (or otherwise inhaled), rectal, or local administration, such as by aerosol or transdermally, for prophylactic and/or therapeutic treatment of atherosclerosis and/or symptoms thereof. The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The peptides and/or peptide mimetics of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent (s).

The excipients are preferably sterile and generally free of undesirable matter. These compositions may be sterilized by conventional, well-known sterilization techniques.

In therapeutic applications, the compositions of this invention are administered to a patient suffering from one or more symptoms of atherosclerosis or at risk for atherosclerosis in an amount sufficient to cure or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of peptide or mimetic can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects.

In certain preferred embodiments, the peptides or peptide mimetics of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other preferred formulations for topical drug delivery include, but are not limited to, ointments and creams. Ointments are semisolid preparations which are typically based on petrolatum or other petroleum derivatives. Creams containing the selected active agent, are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) Biotechnol. Prog. 14: 108; Johnson et al. (1996), Nature Med. 2: 795; Herbert et al. (1998), Pharmaceut. Res. 15, 357) a dry powder composed of biodegradable polymeric microspheres containing the protein in a polymer matrix that can be compounded as a dry formulation with or without other agents.

The ProLease microsphere fabrication process was specifically designed to achieve a high protein encapsulation efficiency while maintaining protein integrity. The process consists of (i) preparation of freeze-dried protein particles from bulk protein by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the protein, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

VII. Lipid-Based Formulations.

In certain embodiments, the peptides of this invention are administered in conjunction with one or more lipids. The lipids can be formulated as an excipient to protect and/or enhance transport/uptake of the peptides or they can be administered separately.

Without being bound by a particular theory, it was discovered of this invention that administration (e.g. oral administration) of certain phospholipids can significantly increase HDL/LDL ratios. In addition, it is believed that certain medium-length phospholipids are transported by a process different than that involved in general lipid transport. Thus, co-administration of certain medium-length phospholipids with the peptides of this invention confer a number of advantages: They protect the phospholipids from digestion or hydrolysis, they improve peptide uptake, and they improve HDL/LDL ratios.

The lipids can be formed into liposomes that encapsulate the polypeptides of this invention and/or they can be complexed/admixed with the polypeptides and/or they can be covalently coupled to the polypeptides. Methods of making liposomes and encapsulating reagents are well known to those of skill in the art (see, e.g., Martin and Papahadjopoulos (1982) J. Biol. Chem., 257: 286–288; Papahadjopoulos et al. (1991) Proc. Natl. Acad. Sci. USA, 88: 11460–11464; Huang et al. (1992) Cancer Res., 52: 6774–6781; Lasic et al. (1992) FEBS Lett., 312: 255–258., and the like).

Preferred phospholipids for use in these methods have fatty acids ranging from about 4 carbons to about 24 carbons in the sn-1 and sn-2 positions. In certain preferred embodiments, the fatty acids are saturated. In other preferred embodiments, the fatty acids can be unsaturated. Various preferred fatty acids are illustrated in Table 3.

TABLE 3

Preferred fatty acids in the sn-1 and/or sn-2 position of the preferred phospholipids for admission of D polypeptides.

| Carbon No. | Common Name | IUPAC Name |
|---|---|---|
| 3:0 | Propionoyl | Trianoic |
| 4:0 | Butanoyl | Tetranoic |
| 5:0 | Pentanoyl | Pentanoic |
| 6:0 | Caproyl | Hexanoic |
| 7:0 | Heptanoyl | Heptanoic |
| 8:0 | Capryloyl | Octanoic |
| 9:0 | Nonanoyl | Nonanoic |
| 10:0 | Capryl | Decanoic |
| 11:0 | Undcanoyl | Undecanoic |
| 12:0 | Lauroyl | Dodecanoic |
| 13:0 | Tridecanoyl | Tridecanoic |
| 14:0 | Myristoyl | Tetradecanoic |
| 15:0 | Pentadecanoyl | Pentadecanoic |
| 16:0 | Palmitoyl | Hexadecanoic |
| 17:0 | Heptadecanoyl | Heptadecanoic |
| 18:0 | Stearoyl | Octadecanoic |
| 19:0 | Nonadecanoyl | Nonadecanoic |
| 20:0 | Arachidoyl | Eicosanoic |
| 21:0 | Heniecosanoyl | Heniecosanoic |

TABLE 3-continued

Preferred fatty acids in the sn-1 and/or sn-2 position of the preferred phospholipids for admission of D polypeptides.

| Carbon No. | Common Name | IUPAC Name |
|---|---|---|
| 22:0 | Behenoyl | Docosanoic |
| 23:0 | Truisanoyl | Trocosanoic |
| 24:0 | Lignoceroyl | Tetracosanoic |
| 14:1 | Myristoleoyl (9-cis) | |
| 14:1 | Myristelaidoyl (9-trans) | |
| 16:1 | Palmitoleoyl (9-cis) | |
| 16:1 | Palmitelaidoyl (9-trans) | |

The fatty acids in these positions can be the same or different. Particularly preferred phospholipids have phosphorylcholine at the sn-3 position.

VIII. Additional Pharmacologically Active Agents.

Additional pharmacologically active agents may be delivered along with the primary active agents, e.g., the peptides of this invention. In one embodiment, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

Suitable beta blockers include, but are not limited to cardioselective (selective beta 1 blockers), e.g., acebutolol (Sectral™), atenolol (Tenormin™), betaxolol (Kerlone™), bisoprolol (Zebeta™), metoprolol (Lopressor™), and the like. Suitable non-selective blockers (block beta 1 and beta 2 equally) include, but are not limited to carteolol (Cartrol™), nadolol (Corgard™), penbutolol (Levatol™), pindolol (Visken™), propranolol (Inderal™), timolol (Blockadren™), labetalol (Normodyne™, Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

Suitable statins include, but are not limited to pravastatin (Pravachol/Bristol-Myers Squibb), simvastatin (Zocor/Merck), lovastatin (Mevacor/Merck), and the like.

Suitable ace inhibitors include, but are not limited to captopril (e.g. Capoten™ by Squibb), benazepril (e.g., Lotensin™ by Novartis), enalapril (e.g., Vasotec™ by Merck), fosinopril (e.g., Monopril™ by Bristol-Myers), lisinopril (e.g. Prinivil™ by Merck or Zestril™ by AstraZeneca), quinapril (e.g. Accupril™ by Parke-Davis), ramipril (e.g., Altace™ by Hoechst Marion Roussel, King Pharmaceuticals), imidapril, perindopril erbumine (e.g., Aceon™ by Rhone-Polenc Rorer), trandolapril (e.g., Mavik™ by Knoll Pharmaceutical), and the like. Suitable ARBS (Ace Receptor Blockers) include but are not limited to losartan (e.g. Cozaar™ by Merck), irbesartan (e.g., Avapro™ by Sanofi), candesartan (e.g., Atacand™ by Astra Merck), valsartan (e.g., Diovan™ by Novartis), and the like.

IX. Kits for the Amelioration of One or More Symptoms of Atherosclerosis.

In another embodiment this invention provides kits for amelioration of one or more symptoms of atherosclerosis or for the prophylactic treatment of a subject (human or animal) at risk for atherosclerosis. The kits preferably comprise a container containing one or more of the peptides or peptide mimetics of this invention. The peptide or peptide mimetic can be provided in a unit dosage formulation (e.g. suppository, tablet, caplet, patch, etc.) and/or may be optionally combined with one or more pharmaceutically acceptable excipients.

The kit can, optionally, further comprise one or more other agents used in the treatment of heart disease and/or atherosclerosis. Such agents include, but are not limited to, beta blockers, vasodilators, aspirin, statins, ace inhibitors or ace receptor inhibitors (ARBs) and the like, e.g. as described above.

In addition, the kits optionally include labeling and/or instructional materials providing directions (i.e., protocols) for the practice of the methods or use of the "therapeutics" or "prophylactics" of this invention. Preferred instructional materials describe the use of one or more polypeptides of this invention to mitigate one or more symptoms of atherosclerosis and/or to prevent the onset or increase of one or more of such symptoms in an individual at risk for atherosclerosis and/or to mitigate one or more symptoms of a pathology characterized by an inflammatory response. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Use of ApoJ-Related Peptides to Mediate Symptoms of Atherosclerosis

Prevention of LDL-Induced Monocyte Chemotactic Activity

FIG. 1 illustrates a comparison of the effect of D-4F (Circulation 2002;105:290–292) with the effect of an apoJ peptide made from D amino acids (D-J336, Ac-LLEQLNEQFNWVSRLANLTEGE-NH$_2$, SEQ ID NO:1) on the prevention of LDL-induced monocyte chemotactic activity in vitro in a co-incubation. Human aortic endothelial cells were incubated with medium alone (no addition), with control human LDL (200 µg protein/ml) or control human LDL+control human HDL (350 µg HDL protein/ml). D-J336 or D-4F was added to other wells in a concentration range as indicated plus control human LDL (200 µg protein/ml). Following overnight incubation, the supernatants were assayed for monocyte chemotactic activity. As shown in FIG. 1, the in vitro concentration of the apoJ variant peptide that prevents LDL-induced monocyte chemotactic activity by human artery wall cells is 10 to 25 times less than the concentration required for the D-4F peptide.

Prevention of LDL-Induced Monocyte Chemotactic Activity by Pre-Treatment of Artery Wall Cells with D-J336

Figure 2:
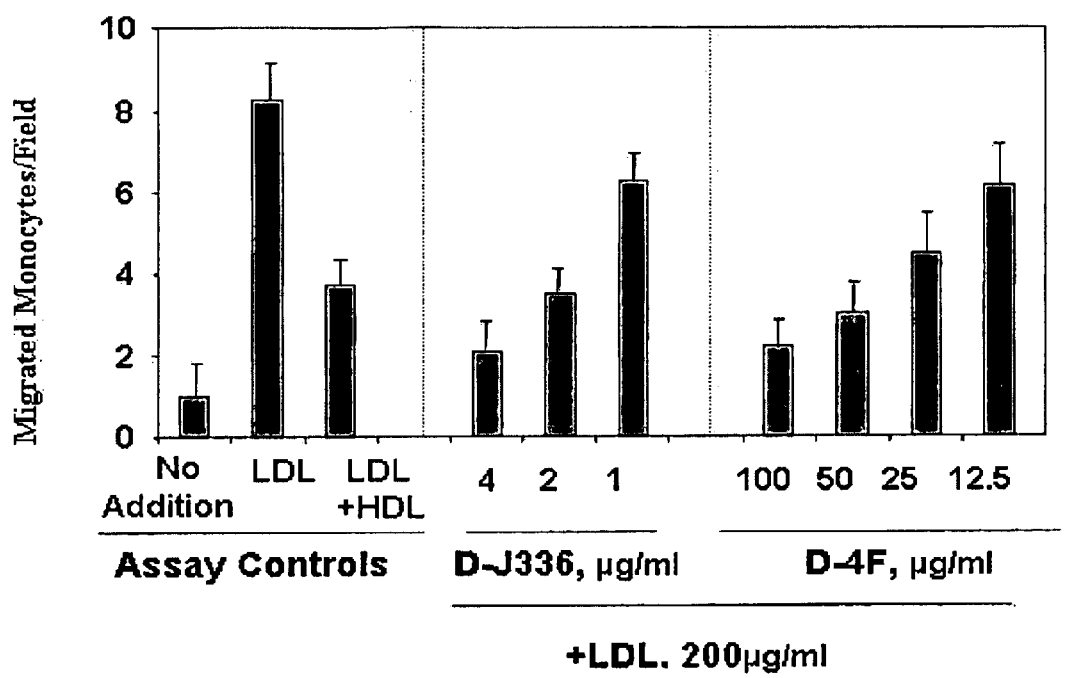
FIG. 2 illustrates the prevention of LDL-induced monocyte chemotactic activity by pre-treatment of artery wall cells with D-J336 as compared to D-4F. The data are mean±SD of the number of migrated monocytes in nine high power fields in quadruple cultures.
Figure 3:
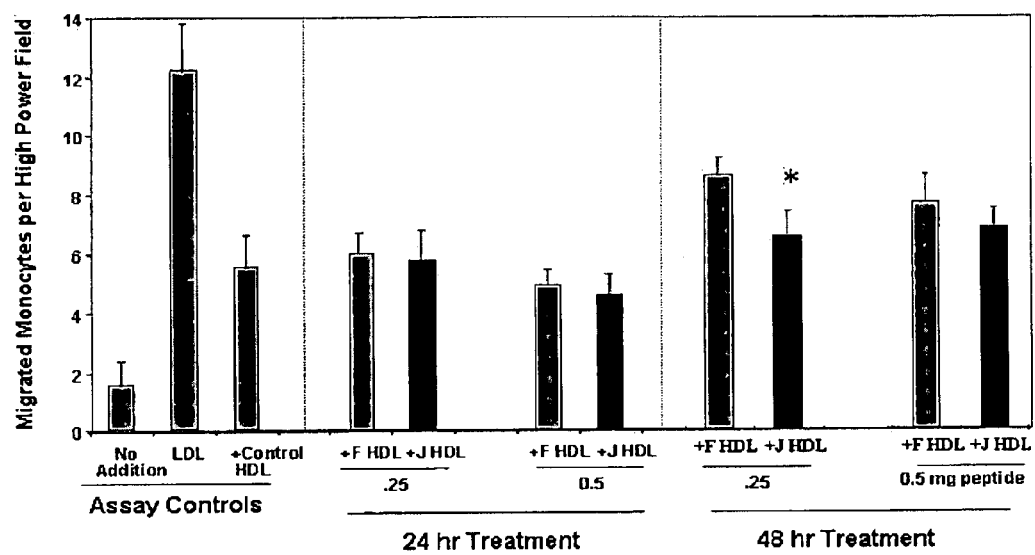
FIG. 3 illustrates he effect of apo J peptide mimetics on HDL protective capacity in LDL receptor null mice. The values are the mean±SD of the number of migrated monocytes in 9 high power fields from each of quadruple assay wells.

FIG. 2 illustrates a comparison of the effect of D-4F with the effect of D-J336 on the prevention of LDL induced monocyte chemotactic activity in a pre-incubation. Human aortic endothelial cells were pre-incubated with D-J336 or D-4F at 4, 2, and 1 µg/ml for DJ336 or 100, 50, 25, and 12.5 µg/ml for D-4F for 6 hrs. The cultures were then washed and were incubated with medium alone (no addition), or with control human LDL (200 μg protein/ml), or with control human LDL+control human HDL (350 μg HDL protein/ml) as assay controls. The wells that were pre-treated with peptides received the control human LDL at 200 μg protein/ml. Following overnight incubation, the supernatants were assayed for monocyte chemotactic activity.

As illustrated in FIG. 2, the ApoJ variant peptide was 10–25 times more potent in preventing LDL oxidation by artery wall cells in vitro.

The Effect of Apo J Peptide Mimetics on HDL Protective Capacity in LDL Receptor Null Mice.

D-4F designated as F, or the apoJ peptide made from D amino acids (D-J336, designated as J) was added to the drinking water of LDL receptor null mice (4 per group) at 0.25 or 0.5 mg per ml of drinking water. After 24- or 48-hrs blood was collected from the mice and their HDL was isolated and tested for its ability to protect against LDL-induced monocyte chemotactic activity. Assay controls included culture wells that received no lipoproteins (no addition), or control human LDL alone (designated as LDL, 200 μg cholesterol/ml), or control LDL+control human HDL (designated as +HDL, 350 μg HDL cholesterol). For testing the mouse HDL, the control LDL was added together with mouse HDL (+F HDL or +J HDL) to artery wall cell cultures. The mouse HDL was added at 100 μg cholesterol/ml respectively. After treatment with either D-4F or D-J336 the mouse HDL at 100 μg/ml was as active as 350 μg/ml of control human HDL in preventing the control LDL from inducing the artery wall cells to produce monocyte chemotactic activity. The reason for the discrepancy between the relative doses required for the D-J336 peptide relative to D-4F in vitro and in vivo may be related to the solubility of the peptides in water and we believe that when measures are taken to achieve equal solubility the D-J peptides will be much more active in vivo as they are in vitro.

Protection Against LDL-Induced Monocyte Chemotactic Activity by HDL from apo E Null Mice given Oral Peptides.

FIG. 4 illustrates the effect of oral apoA-1 peptide mimetic and Apoj peptide on HDL protective capacity. ApoE null mice (4 per group) were provided with D-4F (designated as F) at 50, 30, 20, 10, 5 μg per ml of drinking water or apoJ peptide (designated as J) at 50, 30 or 20 μg per ml of drinking water. After 24 hrs blood was collected, plasma fractionated by FPLC and fractions containing LDL (designated as mlDL for murine LDL) and fractions containing HDL (designated as mHDL) were separately pooled and HDL protective capacity against LDL oxidation as determined by LDL-induced monocyte chemotactic activity was determined. For the assay controls the culture wells received no lipoproteins (no additions), mlDL alone (at 200 μg cholesterol/ml), or mlDL+standard normal human HDL (designated as Cont. h HDL, at 350 μg HDL cholesterol/ml).

For testing the murine HDL, mlDL together with murine HDL (+F mHDL or +J mHDL) were added to artery wall cell cultures. The HDL from the mice that did not receive any peptide in their drinking water is designated as no peptide mHDL. The murine HDL was used at 100 μg cholesterol/ml. After receiving D-4F or D-J336 the murine HDL at 100 μg/ml was as active as 350 μg/ml of normal human HDL. As shown in FIG. 4, when added to the drinking water the D-J peptide was as potent as D-4F in enhancing HDL protective capacity in apo E null mice.

Ability of LDL Obtained from apoE Null Mice Given Oral Peptides to Induce Monocyte Chemotactic Activity.

FIG. 5 illustrates the effect of oral apo A-1 peptide mimetic and apoJ peptide on LDL susceptibility to oxidation. ApoE null mice (4 per group) were provided, in their drinking water, with D-4F (designated as F) at 50, 30, 20, 10, 5 μg per ml of drinking water or the apoJ peptide (D-J336 made from D amino acids and designated as J) at 50, 30 or 20 μg per ml of drinking water. After 24 hrs blood was collected from the mice shown in FIG. 4, plasma fractionated by FPLC and fractions containing LDL (designated as mlDL for murine LDL) were pooled and LDL susceptibility to oxidation as determined by induction of monocyte chemotactic activity was determined. For the assay controls the culture wells received no lipoproteins (no additions), mlDL alone (at 200 μg cholesterol/ml), or mlDL+standard normal human HDL (designated as Cont. h HDL, 350 μg HDL cholesterol).

Murine LDL, mlDL, from mice that received the D-4F (F mlDL) or those that received the apoJ peptide (J mlDL) were added to artery wall cell cultures. LDL from mice that did not receive any peptide in their drinking water is designated as No peptide LDL.

As shown in FIG. 5, when added to the drinking water, D-J336 was slightly more potent than D-4F in rendering the LDL from apo E null mice resistant to oxidation by human artery wall cells as determined by the induction of monocyte chemotactic activity.

Protection Against Phospholipid Oxidation and Induction of Monocyte Chemotactic Activity by HDL Obtained from apo E Null Mice Given Oral Peptides.

FIG. 6 illustrates the effect of oral apoA-1 peptide mimetic and apoj peptide on HDL protective capacity. ApoE null mice (4 per group) were provided with D-4F (designated as F) at 50, 30, 20, 10, 5 μg per ml of drinking water or apoj peptide (D-J336 made from D amino acids and designated as J) at 50, 30 or 20 μg per ml of drinking water. After 24 hrs blood was collected, plasma fractionated by FPLC and fractions containing HDL (designated as mHDL) were pooled and HDL protective capacity against PAPC oxidation as determined by the induction of monocyte chemotactic activity was determined. For the assay controls the culture wells received no lipoproteins (no additions), the phospholipid PAPC at 20 μg/ml+HPODE, at 1.0 μg/ml, or PAPC+HPODE plus standard normal human HDL (at 350 μg HDL cholesterol/ml and designated as +Cont. h HDL).

For testing the murine HDL, PAPC+HPODE together with murine HDL (+F mHDL or +J mHDL) were added to artery wall cell cultures. The HDL from mice that did not receive any peptide in their drinking water is designated as "no peptide mHDL". The murine HDL was used at 100 μg cholesterol/ml.

The data show in FIG. 6 indicate that, when added to the drinking water, D-J336 was as potent as D-4F in causing HDL to inhibit the oxidation of a phospholipid PAPC by the oxidant HPODE in a human artery wall co-culture as measured by the generation of monocyte chemotactic activity Effect of Oral apoA-1 Peptide Mimetic and apoJ Peptide on Plasma Paraoxonase Activity in Mice.

FIG. 7 shows the effect of oral apoA-1 peptide mimetic and apoj peptide on plasma paraoxonase activity in mice. ApoE null mice (4 per group) were provided with D-4F designated as F at 50, 10, 5 or 0 μg per ml of drinking water or apoJ peptide (D-J336 made from D amino acids and designated as J) at 50, 10 or 5 μg per ml of drinking water. After 24 hrs blood was collected and plasma was assayed for PON1 activity. These data demonstrate that, when added to the drinking water, D-J336 was at least as potent as D-4F in increasing the paraoxonase activity of apo E null mice.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated polypeptide that ameliorates a symptom of atherosclerosis or other pathology associated with an inflammatory response, said polypeptide comprising an amphipathic helical peptide having charged residues on the polar face of the peptide and possessing a wide non-polar face, wherein said peptide comprises an amino acid sequence selected from the group consisting of LLEQLNEQFNWVSRLANL (SEQ ID NO:2), and LVGRQLEEFL, (SEQ ID NO:9), and wherein said polypeptide is 40 or fewer amino acids in length and at least 10 amino acids in length.

2. The polypeptide of claim 1, wherein said peptide comprises a G* amphipathic helix.

3. The polypeptide of claim 2, wherein said peptide shows greater than about 50% sequence identity with apo J.

4. The polypeptide of claim 1, wherein said peptide protects a phospholipid against oxidation by an oxidizing agent.

5. The polypeptide of claim 1, wherein said peptide is a concatamer of two or more of said amino acid sequences.

6. The polypeptide of claim 1, wherein said peptide further comprises a protecting group.

7. The polypeptide of claim 1, wherein said peptide further comprises a protecting group coupled to the amino or carboxyl terminus.

8. The polypeptide of claim 6, wherein said protecting group is a protecting group selected from the group consisting of an acetyl, amide, 3 to 20 carbon alkyl groups, Fmoc, 9-fluoreneacetyl group, 1-fluorenecarboxylic group, 9-fluorenecarboxylic, 9-fluorenone-1-carboxylic group, benzyloxycarbonyl, Xanthyl (Xan), Trityl (Trt), 4-methyltrityl (Mtt), 4-methoxytrityl (Mint), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), a propyl group, a butyl group, a pentyl group, a hexyl group, and Trifluoroacetyl (TFA).

9. The polypeptide of claim 6, wherein said peptide comprises a protecting group coupled to the amino terminus and said amino terminal protecting group is a protecting group selected from the group consisting of a benzoyl group, an acetyl, a propionyl, a carbobenzoxy, a propyl, a butyl, a pentyl, a hexyl, and a 3 to 20 carbon alkyl.

10. The polypeptide of claim 6, wherein said peptide comprises a protecting group coupled to the carboxyl terminus and said carboxyl terminal protecting group is an amide.

11. The polypeptide of claim 6, wherein said peptide further comprises:
a first protecting group coupled to the amino terminus wherein said protecting group is a protecting group selected from the group consisting of a benzoyl group, an acetyl, a propionyl, a carbobenzoxy, a propyl, a butyl, a pentyl, a hexyl, and a 3 to 20 carbon alkyl; and
a second protecting group coupled to the carboxyl terminus and said carboxyl terminal protecting group is an amide.

12. The polypeptide of claim 1, wherein said peptide comprises a first protecting group coupled to the amino terminus and a second protecting group coupled to the carboxyl terminus.

13. The polypeptide of claim 1, wherein said polypeptide comprises an Ac group on the amino terminus and an —NH$_2$ on the carboxyl terminus.

14. The polypeptide of claim 1, wherein said peptide comprises a "D" amino acid.

15. The polypeptide of claim 1, wherein said peptide comprises a plurality of "D" amino acids.

16. The polypeptide of claim 1, wherein all enantiomeric amino acids comprising said peptide are "D" amino acids.

17. The polypeptide of claim 1, wherein said polypeptide is mixed with a pharmacologically acceptable excipient.

18. The polypeptide of claim 1, wherein said polypeptide is mixed with a pharmacologically acceptable excipient suitable for oral administration to a mammal.

19. An isolated polypeptide that ameliorates a symptom of atherosclerosis or other pathology associated with an inflammatory response, said polypeptide comprising an amphipathic helical peptide having charged residues on the polar face of the peptide and possessing a wide non-polar face, wherein said polypeptide is coupled to a phospholipid.

20. The polypeptide of claim 19, wherein said polypeptide is covalently coupled to a phospholipid.

21. The polypeptide of claim 19, wherein said polypeptide is covalently coupled to a phospholipid comprising lysophosphatidyl choline.

22. The polypeptide of claim 19, wherein said polypeptide is covalently coupled to a phospholipid comprising a fatty acid selected from the group consisting of propionoyl, butanoyl, pentanoyl, caproyl, heptanoyl, capryloyl, nonanoyl, capryl, undecanoyl, lauroyl, tridecanoyl, myristoyl, pentadecanoyl, palmitoyl, heptadecanoyl, stearoyl, nonadecanoyl, arachidoyl, heniecosanoyl, behenoyl, trucisanoyl, lignoceroyl, myristoleoyl (9-cis), myristelaidoyl (9-trans), palmitoleoyl (9-cis), and palmitelaidoyl (9-trans).

23. The polypeptide of claim 22, wherein said polypeptide is covalently coupled to the sn-1 or sn-2 position of said phospholipid.

24. A composition suitable for oral administration that ameliorates a symptom of atherosclerosis, wherein said composition comprises a peptide comprising an amphipathic helix having charged residues on the polar face of the peptide and possessing a wide non-polar face, wherein said peptide comprises a D amino acid and said peptide is blocked at the amino terminus and the carboxyl terminus.

25. The composition of claim 24, wherein said peptide is at least 10 amino acids in length.

26. The composition of claim 25, wherein said peptide is about 40 or fewer peptides in length.

27. The composition of claim 25, wherein said peptide comprises a G* amphipathic helix.

28. The composition of claim 27, wherein said peptide shows greater than about 50% sequence identity with apo J.

29. The composition of claim 25, wherein said peptide protects a phospholipid against oxidation by an oxidizing agent.

30. The composition of claim 25, wherein said peptide comprises an amino acid sequence selected from the group consisting of LLEQLNEQFNWVSRLANL (SEQ ID NO:2), and LVGRQLEEFL (SEQ ID NO:9).

31. The composition of claim 25, wherein said peptide is blocked at the amino terminus with a first protecting group and said peptide is blocked at the carboxyl terminus with a second protecting group and said first protecting group and said second protecting group are independently selected from the group consisting of an acetyl, amide, 3 to 20 carbon alkyl groups, Fmoc, 9-fluoreneacetyl group, 1-fluorenecarboxylic group, 9-fluorenecarboxylic, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxyberizyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCI-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), a propyl group, a butyl group, a pentyl group, a hexyl group, and Trifluoroacetyl (TFA).

32. The composition of claim 25, wherein said first protecting group is an acetyl.

33. The composition of claim 25, wherein said second protecting group is an amide.

34. The composition of claim 25, wherein more than half of the enantiomeric amino acids comprising said peptide are D amino acids.

35. The composition of claim 25, wherein all enantiomeric amino acids comprising said peptide are D amino acids.

36. The composition of claim 25, wherein said composition further comprises a pharmaceutically acceptable excipient.

37. The composition of claim 36, wherein said excipient is an excipient suitable for oral administration.

38. The composition of claim 36, wherein said excipient is an excipient suitable for injection.

39. A pharmaceutical composition, said composition comprising a polypeptide of any of claims 1, 2, 3, 4, 5, 6, 7, 8, 9, 10, 11, 12, 13, 14, 15, 16, 17, or 18 in a pharmaceutically acceptable excipient.

40. The composition of claim 39, wherein said composition is in the form of a unit dosage formulation.

41. The composition of claim 25, wherein said peptide is coupled to a phospholipid.

42. The composition of claim 41, wherein said peptide is covalently coupled to a phospholipid.

43. The composition of claim 41, wherein said peptide is covalently coupled to a phospholipid comprising lysophosphatidyl choline.

44. The composition of claim 41, wherein said peptide is covalently coupled to a phospholipid comprising a fatty acid selected from the group consisting of propionoyl, butanoyl, pentanoyl, caproyl, heptanoyl, capryloyl, nonanoyl, capryl, undecanoyl, lauroyl, tridecanoyl, myristoyl, pentadecanoyl, palmitoyl, heptadecanoyl, stearoyl, nonadecanoyl, arachidoyl, heniecosanoyl, behenoyl, trucisanoyl, lignoceroyl, myristoleoyl (9-cis), myristelaidoyl (9-trans), palmitoleoyl (9-cis), and palmitelaidoyl (9-trans).

45. The polypeptide of claim 19, wherein said peptide is at least 10 amino acids in length.

46. The polypeptide of claim 19, wherein said peptide is about 40 or fewer amino acids in length.

47. The polypeptide of claim 19, wherein said peptide comprises a G* amphipathic helix.

48. The polypeptide of claim 47, wherein said peptide shows greater than about 50% sequence identity with apo J.

49. The polypeptide of claim 19, wherein said peptide comprises an amino acid sequence selected from the group consisting of LLEQLNEQFNWVSRLANL (SEQ ID NO:2), and LVGRQLEEFL (SEQ ID NO:9).

50. The polypeptide of claim 49, wherein said peptide is a concatamer of two or more of said amino acid sequences.

51. The polypeptide of claim 19, wherein said peptide further comprises a protecting group coupled to the amino or carboxyl terminus.

52. The polypeptide of claim 51, wherein said protecting group is a protecting group selected from the group consisting of an acetyl, amide, 3 to 20 carbon alkyl groups, Fmoc, 9-fluoreneacetyl group, 1-fluorenecarboxylic group, 9-fluorenecarboxylic, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), a propyl group, a butyl group, a pentyl group, a hexyl group, and Trifluoroacetyl (TFA).

53. The polypeptide of claim 51, wherein said peptide comprises a protecting group coupled to the amino terminus and said amino terminal protecting group is a protecting group selected from the group consisting of a benzoyl group, an acetyl, a propionyl, a carbobenzoxy, a propyl, a butyl, a pentyl, a hexyl, and a 3 to 20 carbon alkyl.

54. The polypeptide of claim 51, wherein said peptide comprises a protecting group coupled to the carboxyl terminus and said carboxyl terminal protecting group is an amide.

55. The polypeptide of claim 51, wherein said peptide further comprises:
a first protecting group coupled to the amino terminus wherein said protecting group is a protecting group selected from the group consisting of a benzoyl group, an acetyl, a propionyl, a carbobenzoxy, a propyl, a butyl, a pentyl, a hexyl, and a 3 to 20 carbon alkyl; and
a second protecting group coupled to the carboxyl terminus and said carboxyl terminal protecting group is an amide.

56. The polypeptide of claim 51, wherein said peptide comprises a first protecting group coupled to the amino terminus and a second protecting group coupled to the carboxyl terminus.

57. The polypeptide of claim 51, wherein said peptide comprises an Ac group on the amino terminus.

58. The polypeptide of claim 51, wherein said peptide comprises an —$NH_2$ on the carboxyl terminus.

59. The polypeptide of claim 51, wherein said peptide comprises an Ac group on the amino terminus and an —$NH_2$ on the carboxyl terminus.

60. The polypeptide of claim 51, wherein said peptide comprises a "D" amino acid.

61. The polypeptide of claim 51, wherein said peptide comprises a plurality of "D" amino acids.

62. The polypeptide of claim 51, wherein all enantiomeric amino acids comprising said peptide are "D" amino acids.

63. A method of ameliorating a symptom of atherosclerosis in a mammal, said method comprising administering to said mammal a polypeptide according to any of claims 1, 2, 3, 4, 5–12, 13, 16, 19–23, and 45 62.

64. The method of claim 63, wherein said administering comprises orally administering said polypeptide.

65. The method of claim 63, wherein said mammal is a mammal diagnosed as having one or more symptoms of atherosclerosis.

66. The method of claim 63, wherein said mammal is a mammal diagnosed as at risk for atherosclerosis.

67. The method of claim 63, wherein said mammal is a human.

68. The method of claim 63, wherein said mammal is non-human mammal.

69. A method of ameliorating a symptom of a pathology characterized by an inflammatory response in a mammal, said method comprising administering to said mammal a polypeptide according to any of claims 1, 2, 3, 4, 5–12, 13–16, 19–23, and 45–62.

70. The method of claim 69, wherein said mammal is a mammal diagnosed as having one or more symptoms of an inflammatory response.

71. The method of claim 69, wherein said mammal is a mammal diagnosed as at risk for a pathology associated with an inflammatory response.

72. The method of claim 69, wherein said mammal is a human.

73. The method of claim 69, wherein said mammal is a non-human mammal.

74. A kit for ameliorating a symptom of atherosclerosis, said kit comprising a container containing a polypeptide according to any of claims 2, 3, 4, 5–12, 13–18, 19–23, and 45–62.

75. The kit of claim 74, wherein said polypeptide is combined with a pharmaceutically acceptable excipient in a unit dosage formulation.

76. The kit of claim 75, wherein said unit dosage formulation is for oral administration.

77. The kit of claim 74, further comprising instructional materials teaching the use of said polypeptide or said composition for ameliorating one or more symptoms of atherosclerosis or of a pathology characterized by an inflammatory response.

78. A method of mitigating or preventing a coronary complication associated with an acute phase response to an inflammation in a mammal, wherein said coronary complication is a symptom of atherosclerosis, said method comprising administering to a mammal having said acute phase response or at risk for said acute phase response, a polypeptide according to any of claims 1, 2, 3, 4, 5–12, 13–16, 19–23, and 45–62.

79. The method of claim 78, said administration is by a route selected from the group consisting of oral administration, nasal administration, rectal administration, intraperitoneal injection, intravascular injection, subcutaneous injection, transcutaneous administration, and intramuscular injection.

80. The method of claim 78, wherein said polypeptide is administered in combination with an all L-form of the same polypeptide.

81. The method of claim 78, wherein said polypeptide is provided as a unit formulation in a pharmaceutically acceptable excipient.

82. The method of claim 78, wherein said acute phase response is an inflammatory response associated with a recurrent inflammatory disease.

83. The method of claim 79, wherein said acute phase response is associated with a disease selected from the group consisting of leprosy, tuberculosis, systemic lupus erythematosus, polymyalgia rheumatica, polyarteritis nodosa, scleroderma, idiopathic pulmonary fibrosis, chronic obstructive pulmonary disease, coronary calcification, calcific aortic stenosis, osteoporosis, and rheumatoid arthritis.

84. The method of claim 78, wherein said acute phase response is an inflammatory response associated with a condition selected from the group consisting of a bacterial infection, a viral infection, a fungal infection, an organ transplant, a wound, an implanted prosthesis, parasitic infection, sepsis, endotoxic shock syndrome, and biofilm formation.

85. A method of mitigating or preventing a coronary complication associated with an acute phase response to an inflammation in a mammal, wherein said coronary complication is a symptom of atherosclerosis, said method comprising:

assaying said mammal for an acute phase protein (APP) level indicative of an acute phase response or a significant risk of an acute phase response; and administering to a mammal showing an acute phase protein (APP) level indicative of an acute phase response a polypeptide according to any of claims 1, 2, 3, 4, 5–12, 13–16, 19–23, and 45–62.

86. The method of claim 85, wherein said acute phase protein (APP) is a postive APR selected from the group consisting of serum amyloid A, c-reactive protein, serum amyloid P component, C2 complement protein, C3 complement protein, C4 complement protein, C5 complement protein, C9 complement protein, B complement protein, C1 inhibitor, C4 binding protein, fibrinogen, von Willebrand factor, α1-antitrypsin, α1-antichymotrypsin, α2 antiplasmin, heparin cofactor II, plasminogen activator inhibitor I, haptoglobin, haemopexin, ceruloplasmin, manganese superoxide dismutase, α1-acid glycoprotein, haeme oxygenase, mannose binding protein, leukocyte protein I, lipoprotein (a), and lipopolysaccharide binding protein.

87. The method of claim 85, wherein said acute phase protein (APP) is a negative APR selected from the group consisting of albumin, prealbumin, transferin, apoAI, apoAII, α2-HS glycoprotein, inter-α-trypsin inhibitor, and histidine-rich glycoprotein.

88. The method of claim 63, wherein said polypeptide is in a pharmaceutically acceptable excipient.

89. The method of claim 63, wherein said polypeptide is in a pharmaceutically acceptable excipient suitable for oral administration to a mammal.

90. The method of claim 63, wherein said polypeptide is in a pharmaceutically acceptable excipient in the form of a unit dosage formulation.

91. The method of claim 69, wherein said polypeptide is in a pharmaceutically acceptable excipient.

92. The method of claim 69, wherein said polypeptide is in a pharmaceutically acceptable excipient suitable for oral administration to a mammal.

93. The method of claim 69, wherein said polypeptide is in a pharmaceutically acceptable excipient in the form of a unit dosage formulation.

94. The kit of claim 74, wherein said polypeptide is in a pharmaceutically acceptable excipient.

95. The kit of claim 74, wherein said polypeptide is in a pharmaceutically acceptable excipient suitable for oral administration to a mammal.

96. The kit method of claim 74, wherein said polypeptide is in a pharmaceutically acceptable excipient in the form of a unit dosage formulation.

97. The method of claim 78, wherein said polypeptide is in a pharmaceutically acceptable excipient.

98. The method of claim 78, wherein said polypeptide is in a pharmaceutically acceptable excipient suitable for oral administration to a mammal.

99. The method of claim 78, wherein said polypeptide is in a pharmaceutically acceptable excipient in the form of a unit dosage formulation.

100. The method of claim 85, wherein said polypeptide is in a pharmaceutically acceptable excipient.

101. The method of claim 85, wherein said polypeptide is in a pharmaceutically acceptable excipient suitable for oral administration to a mammal.

102. The method of claim 85, wherein said polypeptide is in a pharmaceutically acceptable excipient in the form of a unit dosage formulation.

* * * * *

```
                           SEQUENCE LISTING

<160> NUMBER OF SEQ ID NOS: 32

<210> SEQ ID NO 1
<211> LENGTH: 22
<212> TYPE: PRT
<213> ORGANISM: Artificial Sequence
<220> FEATURE:
<223> OTHER INFORMATION: Synthetic D peptide.

<400> SEQUENCE: 1

Leu Leu Glu Gln Leu Asn Glu Gln Phe Asn Trp Val Ser Arg Leu Ala
1               5                  10                  15

Asn Leu Thr Glu Gly Glu
            20

<210> SEQ ID NO 2
<211> LENGTH: 18
<212> TYPE: PRT
<213> ORGANISM: Artificial Sequence
<220> FEATURE:
<223> OTHER INFORMATION: Synthetic D peptide.

<400> SEQUENCE: 2

Leu Leu Glu Gln Leu Asn Glu Gln Phe Asn Trp Val Ser Arg Leu Ala
1               5                  10                  15

Asn Leu

<210> SEQ ID NO 3
<211> LENGTH: 25
<212> TYPE: PRT
<213> ORGANISM: Artificial Sequence
<220> FEATURE:
<223> OTHER INFORMATION: Synthetic D peptide.

<400> SEQUENCE: 3

Asn Glu Leu Gln Glu Met Ser Asn Gln Gly Ser Lys Tyr Val Asn Lys
1               5                  10                  15

Glu Ile Gln Asn Ala Val Asn Gly Val
            20                  25

<210> SEQ ID NO 4
<211> LENGTH: 21
<212> TYPE: PRT
<213> ORGANISM: Artificial Sequence
<220> FEATURE:
<223> OTHER INFORMATION: Synthetic D peptide.

<400> SEQUENCE: 4

Ile Gln Asn Ala Val Asn Gly Val Lys Gln Ile Lys Thr Leu Ile Glu
1               5                  10                  15

Lys Thr Asn Glu Glu
            20

<210> SEQ ID NO 5
<211> LENGTH: 32
<212> TYPE: PRT
<213> ORGANISM: Artificial Sequence
<220> FEATURE:
<223> OTHER INFORMATION: Synthetic D peptide.
```

-continued

```
<400> SEQUENCE: 5

Arg Lys Thr Leu Leu Ser Asn Leu Glu Glu Ala Lys Lys Lys Glu
1               5                   10                  15

Asp Ala Leu Asn Glu Thr Arg Glu Ser Glu Thr Lys Leu Lys Glu Leu
            20                  25                  30

<210> SEQ ID NO 6
<211> LENGTH: 16
<212> TYPE: PRT
<213> ORGANISM: Artificial Sequence
<220> FEATURE:
<223> OTHER INFORMATION: Synthetic D peptide.

<400> SEQUENCE: 6

Pro Gly Val Cys Asn Glu Thr Met Met Ala Leu Trp Glu Glu Cys Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic D peptide.

<400> SEQUENCE: 7

Pro Cys Leu Lys Gln Thr Cys Met Lys Phe Tyr Ala Arg Val Cys Arg
1               5                   10                  15

<210> SEQ ID NO 8
<211> LENGTH: 19
<212> TYPE: PRT
<213> ORGANISM: Artificial Sequence
<220> FEATURE:
<223> OTHER INFORMATION: Synthetic D peptide.

<400> SEQUENCE: 8

Glu Cys Lys Pro Cys Leu Lys Gln Thr Cys Met Lys Phe Tyr Ala Arg
1               5                   10                  15

Val Cys Arg

<210> SEQ ID NO 9
<211> LENGTH: 10
<212> TYPE: PRT
<213> ORGANISM: Artificial Sequence
<220> FEATURE:
<223> OTHER INFORMATION: Synthetic D peptide.

<400> SEQUENCE: 9

Leu Val Gly Arg Gln Leu Glu Glu Phe Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic D peptide.

<400> SEQUENCE: 10

Met Asn Gly Asp Arg Ile Asp Ser Leu Leu Glu Asn
1               5                   10
```

```
<210> SEQ ID NO 11
<211> LENGTH: 11
<212> TYPE: PRT
<213> ORGANISM: Artificial Sequence
<220> FEATURE:
<223> OTHER INFORMATION: Synthetic D peptide.

<400> SEQUENCE: 11

Gln Gln Thr His Met Leu Asp Val Met Gln Asp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic D peptide.

<400> SEQUENCE: 12

Phe Ser Arg Ala Ser Ser Ile Ile Asp Glu Leu Phe Gln Asp
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthetic D peptide.

<400> SEQUENCE: 13

Pro Phe Leu Glu Met Ile His Glu Ala Gln Gln Ala Met Asp Ile
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: Synthetic D peptide.

<400> SEQUENCE: 14

Pro Thr Glu Phe Ile Arg Glu Gly Asp Asp Asp
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic D peptide.

<400> SEQUENCE: 15

Arg Met Lys Asp Gln Cys Asp Lys Cys Arg Glu Ile Leu Ser Val
1               5                   10                  15

<210> SEQ ID NO 16
<211> LENGTH: 32
<212> TYPE: PRT
<213> ORGANISM: Artificial Sequence
<220> FEATURE:
<223> OTHER INFORMATION: Synthetic D peptide.

<400> SEQUENCE: 16

Pro Ser Gln Ala Lys Leu Arg Arg Glu Leu Asp Glu Ser Leu Gln Val
1               5                   10                  15

Ala Glu Arg Leu Thr Arg Lys Tyr Asn Glu Leu Leu Lys Ser Tyr Gln
                20                  25                  30
```

```
<210> SEQ ID NO 17
<211> LENGTH: 22
<212> TYPE: PRT
<213> ORGANISM: Artificial Sequence
<220> FEATURE:
<223> OTHER INFORMATION: Synthetic D peptide.

<400> SEQUENCE: 17

Leu Leu Glu Gln Leu Asn Glu Gln Phe Asn Trp Val Ser Arg Leu Ala
 1               5                  10                  15

Asn Leu Thr Gln Gly Glu
            20

<210> SEQ ID NO 18
<211> LENGTH: 11
<212> TYPE: PRT
<213> ORGANISM: Artificial Sequence
<220> FEATURE:
<223> OTHER INFORMATION: Synthetic D peptide.

<400> SEQUENCE: 18

Asp Gln Tyr Tyr Leu Arg Val Thr Thr Val Ala
 1               5                  10

<210> SEQ ID NO 19
<211> LENGTH: 14
<212> TYPE: PRT
<213> ORGANISM: Artificial Sequence
<220> FEATURE:
<223> OTHER INFORMATION: Synthetic D peptide.

<400> SEQUENCE: 19

Pro Ser Gly Val Thr Glu Val Val Val Lys Leu Phe Asp Ser
 1               5                  10

<210> SEQ ID NO 20
<211> LENGTH: 21
<212> TYPE: PRT
<213> ORGANISM: Artificial Sequence
<220> FEATURE:
<223> OTHER INFORMATION: Synthetic D peptide.

<400> SEQUENCE: 20

Pro Lys Phe Met Glu Thr Val Ala Glu Lys Ala Leu Gln Glu Tyr Arg
 1               5                  10                  15

Lys Lys His Arg Glu
            20

<210> SEQ ID NO 21
<211> LENGTH: 26
<212> TYPE: PRT
<213> ORGANISM: Artificial Sequence
<220> FEATURE:
<223> OTHER INFORMATION: Synthetic D peptide.

<400> SEQUENCE: 21

Trp Asp Arg Val Lys Asp Leu Ala Thr Val Tyr Val Asp Val Leu Lys
 1               5                  10                  15

Asp Ser Gly Arg Asp Tyr Val Ser Gln Phe
            20                  25
```

```
<210> SEQ ID NO 22
<211> LENGTH: 25
<212> TYPE: PRT
<213> ORGANISM: Artificial Sequence
<220> FEATURE:
<223> OTHER INFORMATION: Synthetic D peptide.

<400> SEQUENCE: 22

Val Ala Thr Val Met Trp Asp Tyr Phe Ser Gln Leu Ser Asn Asn Ala
 1               5                  10                  15

Lys Glu Ala Val Glu His Leu Gln Lys
            20                  25

<210> SEQ ID NO 23
<211> LENGTH: 27
<212> TYPE: PRT
<213> ORGANISM: Artificial Sequence
<220> FEATURE:
<223> OTHER INFORMATION: Synthetic D peptide.

<400> SEQUENCE: 23

Arg Trp Glu Leu Ala Leu Gly Arg Phe Trp Asp Tyr Leu Arg Trp Val
 1               5                  10                  15

Gln Thr Leu Ser Glu Gln Val Gln Glu Glu Leu
            20                  25

<210> SEQ ID NO 24
<211> LENGTH: 35
<212> TYPE: PRT
<213> ORGANISM: Artificial Sequence
<220> FEATURE:
<223> OTHER INFORMATION: Synthetic D peptide.

<400> SEQUENCE: 24

Leu Ser Ser Gln Val Thr Gln Glu Leu Arg Ala Leu Met Asp Glu Thr
 1               5                  10                  15

Met Lys Glu Leu Lys Glu Leu Lys Ala Tyr Lys Ser Glu Leu Glu Glu
            20                  25                  30

Gln Leu Thr
        35

<210> SEQ ID NO 25
<211> LENGTH: 26
<212> TYPE: PRT
<213> ORGANISM: Artificial Sequence
<220> FEATURE:
<223> OTHER INFORMATION: Synthetic D peptide.

<400> SEQUENCE: 25

Ala Arg Leu Ser Lys Glu Leu Gln Ala Ala Gln Ala Arg Leu Gly Ala
 1               5                  10                  15

Asp Met Glu Asp Val Cys Gly Arg Leu Val
            20                  25

<210> SEQ ID NO 26
<211> LENGTH: 26
<212> TYPE: PRT
<213> ORGANISM: Artificial Sequence
<220> FEATURE:
<223> OTHER INFORMATION: Synthetic D peptide.
```

-continued

```
<400> SEQUENCE: 26

Val Arg Leu Ala Ser His Leu Arg Lys Leu Arg Lys Arg Leu Leu Arg
1               5                   10                  15
Asp Ala Asp Asp Leu Gln Lys Arg Leu Ala
            20                  25

<210> SEQ ID NO 27
<211> LENGTH: 19
<212> TYPE: PRT
<213> ORGANISM: Artificial Sequence
<220> FEATURE:
<223> OTHER INFORMATION: Synthetic D peptide.

<400> SEQUENCE: 27

Pro Leu Val Glu Asp Met Gln Arg Gln Trp Ala Gly Leu Val Glu Lys
1               5                   10                  15
Val Gln Ala

<210> SEQ ID NO 28
<211> LENGTH: 17
<212> TYPE: PRT
<213> ORGANISM: Artificial Sequence
<220> FEATURE:
<223> OTHER INFORMATION: Synthetic D peptide.

<400> SEQUENCE: 28

Met Ser Thr Tyr Thr Gly Ile Phe Thr Asp Gln Val Leu Ser Val Leu
1               5                   10                  15
Lys

<210> SEQ ID NO 29
<211> LENGTH: 22
<212> TYPE: PRT
<213> ORGANISM: Artificial Sequence
<220> FEATURE:
<223> OTHER INFORMATION: Synthetic D peptide.

<400> SEQUENCE: 29

Leu Leu Ser Phe Met Gln Gly Tyr Met Lys His Ala Thr Lys Thr Ala
1               5                   10                  15
Lys Asp Ala Leu Ser Ser
            20

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide linker

<400> SEQUENCE: 30

Gly Gly Gly Gly Ser Ser Ser
1               5

<210> SEQ ID NO 31
<211> LENGTH: 45
<212> TYPE: PRT
<213> ORGANISM: Artificial Sequence
<220> FEATURE:
<223> OTHER INFORMATION: Synthetic D peptide
<220> FEATURE:
<221> NAME/KEY: misc_feature
<223> OTHER INFORMATION: Amino terminus is acylated, carboxyl terminus is amidated
```

-continued

```
<400> SEQUENCE: 31

Leu Leu Glu Gln Leu Asn Glu Gln Phe Asn Trp Val Ser Arg Leu Ala
1               5                   10                  15

Asn Leu Thr Glu Gly Glu Pro Leu Leu Glu Gln Leu Asn Glu Gln Phe
            20                  25                  30

Asn Trp Val Ser Arg Leu Ala Asn Leu Thr Glu Gly Glu
        35                  40                  45

<210> SEQ ID NO 32
<211> LENGTH: 41
<212> TYPE: PRT
<213> ORGANISM: Artificial Sequence
<220> FEATURE:
<223> OTHER INFORMATION: Synthetic D peptide.
<220> FEATURE:
<221> NAME/KEY: misc_feature
<223> OTHER INFORMATION: Amino terminus is acylated, carboxyl terminus is amidated

<400> SEQUENCE: 32

Leu Leu Glu Gln Leu Asn Glu Gln Phe Asn Trp Val Ser Arg Leu Ala
1               5                   10                  15

Asn Leu Thr Glu Gly Glu Pro Asp Trp Phe Lys Ala Phe Tyr Asp Lys
            20                  25                  30

Val Ala Glu Lys Phe Lys Glu Ala Phe
            35                  40
```